US010028971B2

(12) United States Patent
Bird

(10) Patent No.: US 10,028,971 B2
(45) Date of Patent: Jul. 24, 2018

(54) COMPOSITIONS AND METHODS FOR TREATING PSYCHIATRIC DISORDERS

(71) Applicant: GOSFORTH CENTRE (HOLDINGS) PTY LTD., Maroochydore (AU)

(72) Inventor: Philip Bird, Maroochydore (AU)

(73) Assignee: GOSFORTH CENTRE (HOLDINGS) PTY LTD., Maroochydore, Queensland (AU)

(*) Notice: Subject to any disclaimer, the term of this patent is extended or adjusted under 35 U.S.C. 154(b) by 0 days.

(21) Appl. No.: 14/679,559

(22) Filed: Apr. 6, 2015

(65) Prior Publication Data
US 2016/0000815 A1    Jan. 7, 2016

Related U.S. Application Data

(63) Continuation of application No. 13/057,628, filed as application No. PCT/AU2009/001000 on Aug. 6, 2009, now abandoned.

(30) Foreign Application Priority Data

Aug. 6, 2008 (AU) ................ 2008904016
Aug. 6, 2008 (AU) ................ 2008904021

(51) Int. Cl.
*A61K 31/7048* (2006.01)
*A61K 31/137* (2006.01)
*A61K 31/166* (2006.01)
*A61K 31/19* (2006.01)
*A61K 31/35* (2006.01)
*A61K 31/4166* (2006.01)
*A61K 31/4458* (2006.01)

(52) U.S. Cl.
CPC ........ *A61K 31/7048* (2013.01); *A61K 31/137* (2013.01); *A61K 31/166* (2013.01); *A61K 31/19* (2013.01); *A61K 31/35* (2013.01); *A61K 31/4166* (2013.01); *A61K 31/4458* (2013.01)

(58) Field of Classification Search
CPC .............. A61K 31/7048; A61K 31/137; A61K 31/166; A61K 31/19; A61K 31/35; A61K 31/4166; A61K 31/4458
See application file for complete search history.

(56) References Cited

U.S. PATENT DOCUMENTS

| | | | |
|---|---|---|---|
| 2002/0058656 A1 | 5/2002 | Ockert | |
| 2003/0060423 A1 | 3/2003 | Plata-Salaman | |
| 2004/0258758 A1 | 12/2004 | Gustow et al. | |
| 2006/0052428 A1 | 3/2006 | Chez | |
| 2010/0087422 A1 | 4/2010 | Bird | |
| 2011/0065628 A1 | 3/2011 | Johnson et al. | |

FOREIGN PATENT DOCUMENTS

| | | |
|---|---|---|
| EP | 1 600 167 A2 | 11/2005 |
| WO | WO 1993/021910 A1 | 11/1993 |
| WO | WO 2001/039779 A1 | 6/2001 |
| WO | WO 2003/013514 A1 | 2/2003 |
| WO | WO 2003/030899 A2 | 4/2003 |
| WO | WO 2006/120501 A1 | 11/2006 |
| WO | WO 2008/095221 A1 | 8/2008 |
| WO | WO 2004/002462 A1 | 1/2009 |
| WO | WO 2009/014762 A1 | 1/2009 |
| WO | WO 2009/139901 A2 | 11/2009 |
| WO | WO 2010/015029 A1 | 2/2010 |
| WO | WO 2011/100373 A1 | 8/2011 |
| WO | WO 2011/143721 A1 | 11/2011 |

OTHER PUBLICATIONS

Herrmann, "Methylphenidate for the treatment of apathy in Alzheimer disease: prediction of response using dextroamphetamine challenge", J Clin Psychopharmacol. Jun. 2008; 28(3):296-301.*
Dhikav, "Can phenytoin prevent Alzheimer's disease?", Medical Hypotheses (2006) 67, pp. 725-728.*
Tekin, "Antiglutamatergic therapy in Alzheimer's disease—effects of lamotrigine", J Neural Transm (1998) 105, pp. 295-303.*
Loy, "Neuroprotective Properties of Valproate", Journal of Molecular Neuroscience, (2002), 19, pp. 303-307.*
U.S. Appl. No. 13/057,628, filed May 6, 2011.
Baskys et al., *Drug Development Research*, 56: 393-400 (2002).
Bermejo, *Movement Disorders*, 22(14): 2137-2138 (2007).
Chiu et al., *Psychiatry and Clinical Neurosciences*, 61: 630-633 (2007).
Davids et al., *Progress in Neuro-Psychopharmacology & Biological Psychiatry*, 30: 1033-1038 (2006).
Dhikav, *Medical Hypotheses*, 67: 725-728 (2006).
Grunze, *Dialogues Clinical Neuroscience*; 10(1): 77-89 (2008).
Hamrin et al., *Jounal of Child and Adolescent Pychopharmacology*, 11(3): 301-399.
Hill et al., *Movement Disorders*, 18(11): 1301-1371 (2003).
Miyazaki et al., *Brain and Development*, 28: 470-472 (2006).
Reis et al., *Rev Bras Psiquiatr*, 30(2): 132-135 (2008).
Rogawski et al., *Nature Medicine*, 10(7): 685-692 (Jul. 2004).
Schaller et al., *Journal of the American Academy of Child and Adolescent Psychiatry*, 38(2): 112-113 (Feb. 1999).
Scheffer et al., *Am. J. Psychiatry*, 162(1): 58-64 (Jan. 2005).

(Continued)

*Primary Examiner* — Sahar Javanmard
(74) *Attorney, Agent, or Firm* — Leydig, Voit & Mayer, Ltd.

(57) ABSTRACT

Methods of treating psychiatric disorders are provided which include administration of one or more anti-epileptic agents and, optionally, one or more a psychostimulants. Also provided are pharmaceutical compositions comprising, in combination, one or more anti-epileptic agents and one or more psychostimulants. Psychiatric disorders include those associated with impaired cognitive processing, degenerative disorders such as Mild Cognitive Impairment, Parkinson's disease, dementia, non-compliance with therapeutic regimes and eating disorders, although without limitation thereto.

11 Claims, No Drawings

(56) References Cited

OTHER PUBLICATIONS

Schreier, *Journal of Child and Adolescent Pychopharmacology*, 8(1): 49-59 (1998).
Silva et al., *J. Am. Acad. Child Adolesc. Psychiatry*, 35(3): 352-358 (Mar. 1996).
Yitzchak, Frank, *Clinical Electroencephalography*, 24(1): 19-24 (1993).
Zaremba et al., *Pharmacological Reports*, 58: 1-12 (2006).
Australian Patent Office, International Search Report in International Application No. PCT/AU2007/00421 (dated Jun. 29, 2007).
Australian Patent Office, International Search Report in International Application No. PCT/AU2008/000154 (dated Jun. 10, 2009).
Australian Patent Office, International Search Report in International Application No. PCT/AU2009/001000 (dated Oct. 6, 2009).
European Patent Office, Supplementary European Search Report in Europeans Patent Application No. EP 08700447 (dated Mar. 11, 2010).
United Kingdom Patent Office, Search Report in GB Patent Application No. 1111712.4 (dated Oct. 11, 2011).
United Kingdom Patent Office, Search Report in GB Patent Application No. 1111712.4 (dated Feb. 10, 2012).

* cited by examiner

COMPOSITIONS AND METHODS FOR TREATING PSYCHIATRIC DISORDERS

CROSS-REFERENCE TO RELATED APPLICATIONS

This patent application is a continuation of U.S. patent application Ser. No. 13/057,628, filed on May 6, 2011 (abandoned), which is the U.S. national phase of International Patent Application No. PCT/AU2009/001000, filed Aug. 6, 2009, which are incorporated by reference in their entireties herein.

FIELD OF THE INVENTION

THIS INVENTION relates to therapy of psychiatric disorders using anti-epileptic agents, alone or in combination with a psychostimulant. In particular, the invention relates to methods and compositions for treating psychiatric disorders associated with impaired, abnormal or reduced cognitive processing, particularly that which enables higher executive functioning.

BACKGROUND OF THE INVENTION

Cognitive processing enables humans to selectively attend, filter, reflect and prioritise incoming information and integrate this with thoughts and ideas. These processes are particularly important for higher executive function. Executive functions are necessary for goal-directed behavior. They include the ability to initiate and stop actions, to monitor and change behavior as needed, and to plan future behavior when faced with novel tasks and situations. Executive functions include a set of cognitive abilities that control and regulate other abilities and behaviours, to allow humans to anticipate outcomes and adapt to changing situations. Further, the ability to form new concepts and think abstractly is often considered a component of executive function. In particular, this includes the cognitive functions of sequencing, organising and integrating social information and appears to be used during the complex interpersonal interaction which forms the basis of human social communication and interaction. Defective or abnormal cognitive processing can therefore become apparent in behaviours that are controlled by higher executive functioning. Defects in cognitive processing may result in hyper-focusing on a specific topic during conversation and/or an inability to process simultaneously the multiple lines of thought that usually and automatically take place in normal social interaction. Instead the individual may select a preferred, more comfortable, and probably more familiar topic. As a consequence, resistance to or difficulty in following the natural flow of conversation is apparent.

Furthermore, compliance with pharmacotherapy is a long standing and difficult problem with individuals both with and without attention and concentration impairment. Reduced compliance affects and potentially limits the efficacy of all interventions, frequently being the most limiting factor in providing sustained psychotherapeutic benefit. For example, the 12 month compliance rate for use of psycho-stimulants in adults is approximately 33%. The core areas of impairment appear to be in the sequence and organisation of thoughts. This is seen clinically with adults with a diagnosis of attention deficit hyperactivity disorder [(ADHD); a DSM-IV-TR disorder as described in the Fourth Edition of the Diagnostic and Statistical Manual of Mental Disorders (American Psychiatric Association, 2000), and Snyder, Nussbaum, & Robins (Eds.), 2006, ibid (especially Box 2) and Weiss & Murray, 2003] and most commonly treated with psychostimulants. The initial and at times dramatic improvement frequently gives way to a returning disorganisation, and non-adherence with medication and an eventual cessation of treatment. Unless there is a concurrent improvement in the automatic and effortless ability to process social information, the gains in motivation provided by the stimulant will inevitably wane resulting in the associated return of symptoms.

SUMMARY OF THE INVENTION

The present inventor has extended initial observations in treating ADHD and certain other DSM-IV-TR disorders with anti-epileptic agents, alone or in combination with a psychostimulant, to treatment of other psychiatric disorders. Particularly, although not exclusively, the present invention addresses a significant need for effective treatment options for therapy of psychiatric disorders with an underlying defect or abnormality in cognitive processes associated with higher order executive functioning.

In a first aspect the invention provides a method of treating a psychiatric disorder other than epilepsy, bipolar disorder or attention deficit hyperactivity disorder (ADHD), in a subject in need thereof, including the step of administering to the subject one or more anti-epileptic agents, or pharmaceutically acceptable salt thereof, to thereby treat the psychiatric disorder, wherein the amount of anti-epileptic agent is sub-therapeutic for mood stabilization treatment of epilepsy or epileptic symptoms.

In a second aspect, the invention provides one or more anti-epileptic agents, or pharmaceutically acceptable salt thereof, for use in treating a psychiatric disorder other than epilepsy, bipolar disorder or attention deficit hyperactivity disorder (ADHD), wherein the amount of anti-epileptic agent is sub-therapeutic for mood stabilization treatment of epilepsy or epileptic symptoms.

Preferably, the psychiatric disorder of the first and second aspects is not a DSM-IV-TR Communication Disorder, Pervasive Development Disorder or Anxiety Disorder.

In a third aspect, the invention provides a method of treating a psychiatric disorder other than epilepsy, bipolar disorder or attention deficit hyperactivity disorder (ADHD), in a subject in need thereof, including the step of administering to the subject one or more anti-epileptic agents, or pharmaceutically acceptable salt thereof, and one or more psychostimulants, or pharmaceutically acceptable salt thereof, to thereby treat the psychiatric disorder, wherein the amount of anti-epileptic agent is sub-therapeutic for mood stabilization treatment of epilepsy or epileptic symptoms.

In a fourth aspect, the invention provides one or more anti-epileptic agents, or pharmaceutically acceptable salt thereof, and one or more psychostimulants, or pharmaceutically acceptable salt thereof, in combination for use in treating a psychiatric disorder other than epilepsy, bipolar disorder or attention deficit hyperactivity disorder (ADHD), wherein the amount of anti-epileptic agent is sub-therapeutic for mood stabilization treatment of epilepsy or epileptic symptoms.

In one embodiment of the aforementioned aspects, the psychiatric disorder is associated with an impairment or deficiency in higher order executive functioning.

In another embodiment of the aforementioned aspects, the psychiatric disorder is not a developmental disorder or a disorder usually diagnosed in infancy, childhood or adolescence.

In yet another embodiment of the aforementioned aspects, the psychiatric disorder is a degenerative disorder.

In still yet another embodiment of the aforementioned aspects, the psychiatric disorder is a psychotic disorder.

In still yet another embodiment of the aforementioned aspects, the psychiatric disorder is associated with reduced adherence, or non-compliance, with a medication regime that includes the administration of a therapeutic agent other than, or in addition to, a psychostimulant.

In a further embodiment of the aforementioned aspects, the psychiatric disorder is an eating disorder.

In certain particular embodiments, the psychiatric disorder is selected from the group consisting of: degenerative disorders and/or movement disorders such as Parkinson's disease, dementia and Mild Cognitive Impairment; addiction; reduced adherence, or non-compliance, with a medication regime; eye gaze-associated disorders, dysthymia; psychotic disorders such as schizophrenia; eating disorders such as Anorexia Nervosa and Bulimia Nervosa; sleep disorders; developmental dyspraxia; Tourette's syndrome, and personality disorders.

One particular embodiment of the aforementioned methods includes, prior to administration of the anti-epileptic agent alone or in combination with the psychostimulant, a step of determining whether said subject is, or may be, in need of prophylactic or therapeutic treatment for said psychiatric disorder. This step may be performed by clinical assessment, genetic testing or genetic counseling, alone or in combination.

In a fifth aspect, the invention provides a pharmaceutical composition comprising, in combination, one or more anti-epileptic agents, or a pharmaceutically acceptable salt thereof, and one or more psychostimulants, or pharmaceutically acceptable salt thereof; together with a pharmaceutically acceptable carrier, diluent and/or excipient.

In a sixth aspect, the invention provides a pharmaceutical kit comprising a first pharmaceutical composition comprising (i) one or more anti-epileptic agent or a pharmaceutically acceptable salt thereof, together with a pharmaceutically acceptable carrier, diluent and/or excipient; and (ii) a second pharmaceutical composition comprising one or more psychostimulants together with a pharmaceutically acceptable carrier, diluent and/or excipient.

Preferably the first pharmaceutical composition is provided as a dosage unit containing a dose of anti-epileptic agent which is sub-therapeutic for mood stabilization or epilepsy.

The kit may also include instructions for use of the combination of the first and second pharmaceutical compositions according to a method of the invention.

It will be appreciated that according to each of the aforementioned aspects, the anti-epileptic agent(s) or pharmaceutically acceptable salt thereof is present, or administered, in amount that is sub-therapeutic as a total daily dose typically effective in mood stabilization or in treatment of epilepsy or epileptic symptoms when administered alone.

In preferred embodiments, the amount of anti-epileptic agent(s) is less than 50% of the daily dose of anti-epileptic agent typically effective in mood stabilization or in treating epilepsy or epileptic symptoms when used alone. In particular embodiments, the amount of anti-epileptic agent is less than 40%, 30%, 20%, or 10% of the daily dose of anti-epileptic agent typically effective in mood stabilization or in treating epilepsy or epileptic symptoms when used alone.

In further preferred embodiments, the ratio of anti-epileptic agent to psychostimulant may be from about 1:800 to 800:1, about 1:400 to 400:1, about 1:100 to 100:1, about 1:10 to 10:1, about 1:5 to 5:1, about 1:4 to 4:1, about 1:3 to 3:1, about 1:2 to 2:1, or about 1:1

In other preferred embodiments, the respective amounts of anti-epileptic agent and psychostimulant may be (a) from about 0.1 mg to 50 mg sodium valproate, or a derivative thereof, and from 0.1 to 20 mg dextroamphetamine sulphate; (b) from about 1 mg to 400 mg sodium valproate, or a derivative thereof, and from 1 to 200 mg dextroamphetamine sulphate; (c) from about 0.5 mg to 80 mg topiramate and from 1 to 400 mg methylphenidate; (d) from about 0.5 mg to 80 mg topiramate and from 1 to 200 mg dextroamphetamine sulphate; (e) from about 0.25 mg to 80 mg phenytoin and from 1 to 400 mg methylphenidate; (f) from about 0.25 mg to 80 mg phenytoin and dextroamphetamine sulphate from about 1 to 200 mg; (g) from about 0.5 mg to 200 mg rufinamide and from 1 to 400 mg methylphenidate; (h) from about 0.5 mg to 200 mg rufinamide and from 1 to 200 mg dextroamphetamine sulphate; (A) from about 1 mg to 400 mg sodium valproate, or a derivative thereof, and from about 1 to 80 mg phenytoin and from about 1 to 200 mg dextroamphetamine sulphate; (B) from about 1 mg to 2000 mg sodium valproate, or a derivative thereof, and from about 1 to 80 mg Phenytoin and from about 1 to 200 mg dextroamphetamine sulphate; (C) from about 1 mg to 2000 mg sodium valproate, or a derivative thereof, and from about 1 to 80 mg Topiramate and from about 1 to 200 mg dextroamphetamine sulphate; or (D) from about 1 mg to 2000 mg sodium valproate, or a derivative thereof, and from about 1 to 80 mg Phenytoin and from about 1 to 400 mg methylphenidate.

In additional aspects, the invention provides methods and pharmaceutical compositions for treating psychiatric disorders wherein a combination of an anti-epileptic agent and a non-stimulant are administered to a subject, or are present in the pharmaceutical composition.

DETAILED DESCRIPTION

In initial work, the present inventor demonstrated that low-dose anti-epileptic agents, alone or in combination with a psychostimulant, were effective in treating ADHD, which is a neurobehavioral developmental disorder distinguished by symptoms of inattention, hyperactivity and impulsivity. Although ADHD is one of the most frequently diagnosed psychological disorders in childhood, long-term studies have demonstrated that symptoms are often maintained into adulthood [see Fourth Edition of the Diagnostic and Statistical Manual of Mental Disorders (American Psychiatric Association, 2000), referred to as DSM-IV-TR. See also Snyder, Nussbaum, & Robins (Eds.), 2006, ibid (especially Box 2) and Weiss & Murray, 2003, ibid].

Treatment with low-dose anti-epileptic agents was also found to be useful in treatment of Communication Disorders; Pervasive Development Disorders and Anxiety Disorders, particularly those that fall within the DSM-IV-TR classification: Communication Disorders (e.g. Expressive Language Disorder, Mixed Receptive-Expressive Language Disorder, Phonological Disorder, Stuttering, Communication Disorder NOS (=Not Otherwise Specified); Pervasive Development Disorders (Autistic Spectrum Disorders such as Autistic Disorder and Asperger's Disorder; Rett's Disorder, Childhood Disintegrative Disorder and Pervasive Developmental Disorder NOS); and Anxiety Disorders (e.g. Generalized Anxiety Disorder).

Treatment with low-dose anti-epileptic agents, alone or in combination with psychostimulants was also demonstrated to improve reading comprehension and/or reading fluency associated with learning difficulties, treat ocularmotor dysfunction associated with learning difficulties, treat abnormal saccadic eye movements and improve cerebellar-mediated motor planning and sequencing.

Accordingly, the present invention extends the therapeutic uses of anti-epileptic agents, alone or in combination with psychostimulants, beyond ADHD and/or DSM-IV-TR Communication Disorders, Pervasive Development Disorders and Anxiety Disorders, particularly to psychological disorders with an underlying defect or abnormality in cognitive processes associated with higher order executive functioning, although without limitation thereto.

Therefore, in one particular form, the present invention relates to a method for the treatment of a subject with a psychological disorder other than ADHD, bipolar disorder, epilepsy and Communication Disorders; Pervasive Development Disorders and Anxiety Disorders, particularly those that fall within the DSM-IV-TR classification referred to above, wherein the method includes administration of one or more anti-epileptic agents to the subject.

In another particular form, the invention relates a method for co-therapy of a subject with a psychological disorder other than ADHD, epilepsy or bipolar disorder wherein the method includes administration of one or more anti-epileptic agents in combination with one or more psychostimulant agents to the subject.

Preferably, these methods are not for the purpose of improving reading comprehension and/or reading fluency associated with learning difficulties, treating ocularmotor dysfunction associated with learning difficulties, treating abnormal saccadic eye movements or improving cerebellar-mediated motor planning and sequencing.

In a further particular form, the invention provides particular combinations of one or a plurality of anti-epileptic agents with one or a plurality of psychostimulants. Such compositions may be useful in treating psychological disorders including ADHD, bipolar disorder and other DSM-IV-TR disorders as referred to above, as well as other psychological disorders, particularly those with an underlying defect or abnormality in cognitive processes associated with higher order executive functioning, and any other psychiatric disorder described herein. These pharmaceutical compositions may also help to improve reading comprehension and/or reading fluency associated with learning difficulties, treat ocularmotor dysfunction associated with learning difficulties, treat abnormal saccadic eye movements and improve cerebellar-mediated motor planning and sequencing and the prodromal symptoms of later serious psychiatric disorders.

Unless defined otherwise, all technical and scientific terms used herein have the same meaning as commonly understood by one of ordinary skill in the art (e.g. in pharmaceutical chemistry and medicine, including psychiatry).

Unless contraindicated or noted otherwise, in these descriptions and throughout this specification, the terms "a" and "an" mean one or more, the term "or" means and/or.

Unless defined otherwise, all technical and scientific terms used herein have the same meaning as commonly understood by one of ordinary skill in the art (e.g. in pharmaceutical chemistry.

By "comprising" is meant including, but not limited to, whatever follows the word "comprising". Thus, use of the term "comprising" indicates that the listed elements are required or mandatory, but that other elements are optional and may or may not be present.

By "consisting of" is meant including, and limited to, whatever follows the phrase "consisting of." Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, "subject" or "individual" or "patient" refers to any subject for whom or which therapy is desired, and generally refers to the recipient of the therapy to be practiced according to the invention. The subject can be any vertebrate, but will preferably be a mammal. If a mammal, the subject will preferably be a human, but may also be a domestic livestock, laboratory subject or pet animal. The subject is most preferably a human adult, child or infant, who is or has been the object of treatment, observation or experiment.

As used herein, unless the context demands otherwise, the term "treat," "treating," or "treatment" as used herein means to counteract a medical condition (e.g., a psychological disorder) to the extent that the medical condition is improved according to clinically acceptable standard(s). For example, "to treat a psychological disorder" means to improve the disorder or relieve symptoms of the particular disorder in a patient, wherein the improvement and relief are evaluated with a clinically acceptable standardized test (e.g., a patient self-assessment scale) and/or an empirical test. "Treat," "treating," or "treatment" as used herein also includes prophylactic treatment unless the context requires otherwise.

As used herein, the term "active agent" or "agent" means any substance which can affect any physical or biochemical properties of a biological system, pathway, molecule, or interaction relating to an organism, including but not limited to animals and humans. In particular, as used herein, agents include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes and small molecule drugs. Classes of active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

Certain agents, biologically-active molecules and other active compounds according to this invention may exist as enantiomers. Where they possess two or more chiral centers, they may additionally exist as diastereomers. It is to be understood that all such isomers and mixtures thereof are encompassed within the scope of the present invention. Furthermore, some of the crystalline forms for the agents or compounds may exist as polymorphs and as such are intended to be included in the present invention. In addition, some of the agents or compounds may form solvates with water (i.e., hydrates) or common organic solvents, and such solvates are also intended to be encompassed within the scope of this invention.

As used herein, the terms "co-therapy" and "combination therapy" shall mean treatment of a subject in need thereof by administering one or more anti-epileptic agent(s) and one or more psychostimulant(s), wherein the psychostimulant(s) and the anticonvulsant or anti-epileptic agent(s) are administered by any suitable means, simultaneously, sequentially, separately or in a single pharmaceutical formulation or combination. Where the psychostimulant(s) and the anticonvulsant or anti-epileptic agent(s) are administered in separate dosage forms, the number of dosages administered per day for each compound may be the same or different. The psychostimulant(s) and the anticonvulsant or anti-epileptic agent(s) may be administered via the same or different routes of administration.

The term "effective amount" or "therapeutically effective amount" means that amount of active compound that elicits the biological or medicinal response in a tissue system, animal or human that is being sought by a researcher, veterinarian, medical doctor or other clinician, which includes alleviation of one or more of the symptoms of the disease or disorder being treated; reduction of the severity of one or more of the symptoms of the disease or disorder being treated; or otherwise provides the desired effect. The precise dosage will vary according to a variety of factors such as subject-dependent variables (e.g., age, medical history, etc.), the disorder or condition, and the treatment being affected. In particular aspects of the present invention directed to co-therapy or combination therapy, comprising administration of one or more anti-epileptic agents and one or more psychostimulant agents, therapeutically effective amount means that amount of the combination of agents taken together so that the combined effect elicits the desired biological or medicinal response. For example, the therapeutically effective amount of co-therapy comprising administration of a psychostimulant and at least one suitable anti-epileptic agent would be the amount of the psychostimulant and the amount of the suitable anti-epileptic agent that, when taken together or sequentially, have a combined effect that is therapeutically effective. Further, it will be recognized by one skilled in the art that in the case of co-therapy with a therapeutically effective amount, as in the example above, the amount of psychostimulant or the amount of the suitable anti-epileptic agent individually may or may not be therapeutically effective.

As used herein, unless otherwise noted, the term "anti-epileptic agent" and the abbreviation "AED" will be used interchangeably with the terms "anti-convulsant agent", "anticonvulsant" "antiepileptic mood stabilizer", "mood stabilizer", and "antiepileptic" and as used herein, refer to an agent capable of treating, inhibiting or preventing seizure activity or ictogenesis when the agent is administered to a subject or patient.

While not wishing to be bound by any particular theory, it is believed that the exact chemical class of AED is not determinative of the utility of any specific AED in the compositions and methods of the invention. Rather, it is the efficacy of AEDs in treatment of epileptic, pre-epileptic, or ictogenic events, convulsions, mood stabilization that identifies the relevant compounds or agents useful within the invention. Thus, AEDs of diverse chemical classes are useful and relevant (with suitable adjustments of dose) alone or in combination with similarly diverse classes of psychostimulants within the scope of the invention. In particular, the combination therapy of the invention will be more effective at treating particular psychological disorders in part because the combinations have been found to be surprisingly effective in treating underlying cognitive dysfunctions or impairments. Indeed, clinical examples are provided that demonstrate effectiveness and relevance of diverse classes of AEDs in combination with diverse classes of psychostimulants.

Particular examples of AEDs include sodium valproate (sodium di-n-propylacetic acid) and derivatives thereof (valproic acid, valproate pivoxil, semisodium valproate, divalproex, valproylamides such as valpromide, Depakene, Depakote, Depakote ER), tiagabine, ethosuximide, zonisamide, carbamazepine, oxcarbazepine, lamotrigine, tiagabine, gabapentin, pregabalin, phenytoin, primidone, phenobarbitone, phenobarital, topiramate, diazepam and related compounds, and levetiracetam.

In particular embodiments the AED is selected from the group consisting of brivaracetam, carbamazepine, clobazam, clonazepam, ethosuximide, felbamate, gabapentin, lacosamide, lamotrigine, levetiracetam, oxcarbazepine, phenobarbital, phenytoin, pregabalin, primidone, retigabine, rufinamide, safmamide, seletracetam, talampanel, tiagabine, topiramate, valproate, vigabatrin, zonisamide, benzodiazepines, barbiturates and sedative hypnotics.

Particularly preferred AEDs are sodium valproate and derivatives thereof, tiagabine, topiramate, carbamazepine, oxcarbazepine, ethotoin, phenytoin, gabapentin, pregabalin, and rufinamide. In another embodiment, the anti-convulsant or anti-epileptic agent(s) is selected from the group consisting of carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate, vigabatrin and zonisamide.

In another embodiment, the anti-convulsant or anti-epileptic agent(s) is selected from the group consisting of carbamazepine, lamotrigine, phenobarbital, phenytoin, topiramate, valproate and zonisamide. Preferably, the anti-convulsant or anti-epileptic agent(s) is selected from the group consisting of carbamazepine, gabapentin, lamotrigine, levetiracetam, oxcarbazepine, phenytoin, pregabalin, rufinamide, valproate and topiramate. More preferably, the anticonvulsant or anti-epileptic is selected from the group consisting of gabapentin, lamotrigine, levetiracetam, pregabalin, rufinamide, valproate and topiramate. In a further embodiment, the anti-epileptic is selected from the group consisting of valproate, rufinamide, topiramate, and phenytoin.

In particular embodiments, examples of anti-convulsant or anti-epileptic agents include, but are not limited to, the following, described non-exclusively by either mode of action or chemical class:

(a) AMPA antagonists such as AMP-397, E-2007, NS-1209, talampanel, perampanel, and the like;

(b) Benzodiazepines such as diazepam, lorazepam, clonazepam, clobazam, clorazepate, midazolam, nimetazepam, nitrazepam, temasepam, and the like;

(c) Barbiturates such as phenobarbital, amobarbital, methylphenobarbital, primidone, Barbexaclone sodium, metharbital, pentobarbital, and the like;

(d) Valproates (including fatty acid derivatives) such as valproic acid, valproate semisodium, valpromide, divalproex, valnoctamide, and the like;

(e) GABA related agents such as gabapentin (2-[1-(aminomethyl)cyclohexyl]acetic acid), pregabalin ((S)-3-(aminomethyl)-5-methylhexanoic acid), vigabatrin, and the like;

(f) AEDs such as losigamone, retigabine, rufinamide (1-[(2,6-difluorophenyl)methyl]triazole-4-carboxamide), SPD-421 (DP-VPA), T-2000, XP-13512, and the like;

(g) Iminostilbenes such as carbamazepine, oxcarbazepine, and the like;

(h) Hydantoins such as phenytoin sodium, Phenytoin, mephenytoin, fosphenytoin sodium, ethotoin, and the like;

(h) NMDA antagonists such as harkoseride, and the like;

(i) Sodium channel blockers such as BIA-2093, CO-102862, lamotrigine, and the like;

(j) Succinimides such as methsuximide, ethosuximide, and the like;

(k) Carboxylic acids such as tiagabine, and the like;

(l) AEDS such as acetazolamide, clomthiazole edisilate, zonisamide, felbamate, topiramate, tiagabine, levetiracetam, briveracetam, GSK-362115, GSK-406725, ICA-69673, CBD cannabis derivative, isovaleramide (NPS-1776), RWJ-333369 (carisbamate), safinamide, seletracetam, soretolide, stiripentol, valrocemide, and the like;

(m) oxazolidinediones such as trimethadione, paramethadione, ethadione and the like;

(n) succinimides such as ethosuximide, phensuximide, mesuximide, and the like;

(o) pyrrolidines such as levetiracetam, and the like;

(p) sulphonamides, such as acetazolamide, methazolamide, zonisamide, sultiame, and the like;

(q) aminobutyric acids and the like;

(r) sulfamate-substituted monosaccharides such as topiramate (2,3:4,5-Bis-O-(1-methylethylidene)-beta-D-fructopyranose sulfamate)), and the like;

(s) carboxamides such as carbamazepine, oxcarbazepine, rufmamide, and the like;

(t) aromatic allylic alcohols such as stiripentol, and the like;

(u) ureas such as phenacemide, pheneturide, and the like;

(v) phenyltriazines such as lamotrigine, and the like;

(w) carbamates such as emylcamate, felbamate, meprobamate, and the like;

(x) pyrrolidines such as brivaracetam, levetriacetame, nefiracetam, selectracetam, and the like; and (xi) Eugenols such as (4-Allyl-2-Methoxyphenol). Phenyleugenol, Benzyleugenol, and phenylethyleugenol.

In one embodiment, the mood stabiliser is a gamma-aminobutyric acid (GABA) enhancer, i.e. a GABAergic agent.

In further examples, a variety of AEDs have been described in the art and useful as anti-epileptics and mood stabilizers. For example, those mentioned in the following published patents or patent applications describe, in relation to the agent they disclose, both suitable methods for their preparation and doses for their administration. These publications are herein incorporated by reference.

EP-0021121-A discloses a group of 3,5-diamino-6-(substituted phenyl)-1,2,4-triazines which are active in the treatment of central nervous system (CNS) disorders, for example in the treatment of epilepsy. One such triazine is 3,5-diamino-6-(2,3-dichlorophenyl)-1,2,4-triazine which is alternatively called lamotrigine. EP-0372934-A discloses pyrimidine compounds useful in the treatment of CNS disorders. Example 18 of EP-0372934-A discloses 2,4-diamino-5-(2,3-dichlorophenyl)-6-fluoromethyl pyrimidine.

WO 97/09317 discloses the R(−) enantiomer of this compound, R(−)-2,4-diamino-5-(2,3-dichlorophenyl)-6-fluoromethyl pyrimidine, substantially free of the corresponding S(+)enantiomer. WO98/38174 discloses pyrazine derivatives, including rufmamide, useful in the treatment of CNS disorders such as epilepsy. WO99/32462 relates to a triazine compound which is useful in the treatment of central nervous system (CNS) diseases and disorders, i.e. the compound 5-amino-6-[2,3,5-trichlorophenyl]-1,2,4-triazine and pharmaceutically acceptable derivatives thereof. WO00/12488 relates to pyrazine compounds useful in the treatment of CNS diseases and resulting disorders.

As used herein, unless otherwise noted, the term "psychostimulant" or "psychostimulant agent" and the terms "central nervous system stimulant" and "CNS stimulant" will be used interchangeably and refer to an agent capable of producing an increase or enhancement in psychomotor activity. However, and as known to those of skill in the art and as herein defined, the terms "psychostimulant" and "CNS stimulant" as used herein do not refer to agents such as caffeine and nicotine, which are not considered to be psychostimulants, at least because they do not enhance locomotor behavior in rodents (Sulzer, D., et al. Prog. Neurobio. 75(6): 406-433).

A large number of psychostimulants are known in the art and suitable for use in the invention. While not wishing to be bound by any particular theory, it is believed that the exact chemical class of psychostimulant is not determinative of the utility of any specific psychostimulant in the compositions and methods of the invention. Rather, it is the efficacy of psychostimulants in increasing or enhancing psychomotor activity that is encompassed by the invention. Thus, psychostimulants of diverse chemical classes are equally useful and relevant (with suitable adjustments of dose) in combination with similarly diverse classes of AEDs within the scope of the invention. Indeed, clinical examples are provided that demonstrate effectiveness and relevance of diverse classes of psychostimulants in combination with diverse classes of AEDs.

Psychostimulants useful for the compositions on the invention include, but are not limited to: methylphenidate (Ritalin) administered at about 0.01 to about 2.5 mg/kg/day; dextroamphetamine (Dexedrine) administered at about 0.07 to about 1.5 mg/kg/day; amphetamine (Adderall) administered at about 0.05 to about 1.5 mg/kg/day; and pemoline (Cylert) administered at about 0.1 to about 2.0 mg/kg/day.

Examples of psychostimulants with use in the invention include the class of compounds identifiable as amphetamines. The term "amphetamine" as understood by those of skill in the art, typically contains an alpha-methyl-phenethyl-amine motif. Exemplary amphetamines are amphetamine, methamphetamine, and dextroamphetamine or "dexamphetamine". Dextroamphetamine or "D-amphetamine" or "dexamphetamine" is the dextrorotary (D) stereoisomer of amphetamine. Amphetamines in pharmaceutical form include, for example, dextroamphetamine sulphate (Dexamin™, Dextrostat™, Dexadrine™), dexamphetamine or mixed amphetamine salts (Adderall XR™)) and pemoline (Cylert™)).

Methylphenidate is typically formulated for pharmaceutical use as the hydrochloride (e.g. Ritalin™, Ritaline LA™, Focalin™, Concerta™, Methylin, Attenta™, Lorentin™, Daytrana™, Tranquilyn™, Equasym™, Riphenidate™ Rubifen™, Metadate CD™ Biphentin™). Methylphenidate is described in U.S. Pat. No. 2,957,880 and Biphentin™ in Canadian Patents 2355854 and 2355644. Though not technically an amphetamine, methylphenidate functions in a similar way in the CNS or brain. Methylphenidate typically has a relatively short duration of action (2 to 4 hours). Hence, slow release or continual release formulations or methods of delivery have been developed, e.g. Concerta™ and the transdermal patch, marketed as Daytrana™. Further examples of slow or controlled release formulations are known in the art, for example as described in published US patent application no. 2007/0059349.

Typical doses for these medications are described in Wilens and Dodson, 2004, Clin. Psychiatry 65: 1301-1313 (methylphenidate—juveniles: 0.6 to 1.0 mg/kg/day; adults 20 to 100 mg per day, amphetamine—juveniles: 0.3 to 1.5 mg/kg/day; adults 10 to 70 mg/day, pemoline—juveniles: 1.0 to 3.0 mg/kg/day; adults 75 to 150 mg/day).

Additional examples useful in the invention include: Eugeroics such as Adrafinil, Armodafinil, Carphedon, Modafinil; Phenethylamines such as 4-Fluoroamphetamine, 4-Fluoromethamphetamine, 4-Methylmethcathinone, 4-MTA, α-PPP, Amphechloral, Amphetamine (Dextroamphetamine, Adderall), Amphetaminil, Benzphetamine, Bupropion, Cathinone, Chlorphentermine, Clobenzorex, Clortermine, Cypenamine, Diethylpropion, Dimethoxyamphetamine, Dimethylamphetamine, Dimethylcathinone, Diphenyl prolinol, Ephedrine, Epinephrine, Ethcathinone, Ethylamphetamine, Fencamfamine, Fenethylline, Fenfluramine, Fenproporex, Feprosidnine, Furfenorex, Levomethamphetamine, Lisdexamfetamine (Vyvance™) (L-lysine-d-amphetamine), MDMA, Mefenorex, Methamphetamine, Methcathinone, Methoxyphedrine, Methylone, Octopamine, Parahydroxyamphetamine, PMA, PMEA, PMMA, PPAP, Phendimetrazine, Phemnetrazine, Phentermine, Phenylephrine, Phenylpropanolamine, Prolintane, Propylamphetamine, Pseudoephedrine, Selegiline, Synephrine, Tenamphetamine, Xylopropamine; Piperazines such as BZP, MeOPP, MBZP, mCPP, 2C-B-BZP; Xanthines such as Aminophylline, Paraxanthine, Theobromine, Theophylline; Tropanes such as Brasofensine, CFT, Cocaethylene, Cocaine, Dimethocaine, Lometopane, PIT, PTT, RTI-121, Tesofensine, Troparil, WF-23, WF-33; Cholinergics such as Arecoline, Cotinine; Convulsants such as Bicuculline, Gabazine, Pentetrazol, Picrotoxin, Strychnine, Thujone; Phenylaminooxazoles such as 4-Methyl-aminorex, Aminorex, Clominorex, Fenozolone, Fluminorex, Pemoline, Thozalinone; Others such as Amantadine, Amineptine, Bemegride, BPAP, Clenbuterol, Clofenciclan, Cyclopentamine, Cyprodenate, Desoxypipradrol, Ethylphenidate, Ethamivan, Gilutensin, GYKI-52895, Hexacyclonate, Indanorex, Indatraline, Isometheptene, Mazindol, MDPV, Mesocarb, methylphenidate, Dexmethylphenidate, Naphthylisopropylamine, Nikethamide, Nocaine, Nomifensine, Phacetoperane, Phthalimidopropiophenone, Pipradrol, Prolintane, Propylhexedrine, Pyrovalerone, Tuamine, Vanoxerine, Yohimbine, Zylofuramine, Deanol, Diethylaminoethanol, Dimefline Hydrochloride, Etilamfetamine Hydrochloride, Fencamfamin Hydrochloride, Fenetylline Hydrochloride, Fenfluramine Hydrochloride, Fenproporex Hydrochloride, Lobeline Hydrochloride, Pentetrazol, Propylhexedrine.

Combinations of two or more psychostimulants may be used. References to all psychostimulant described herein include pharmaceutically acceptable salts thereof, as appropriate, and slow release and extended release formulations, as well as prodrugs of the listed active agents. An example of such a prodrug is lisdexamfetamine (L-lysine-d-amphetamine).

Therapeutic Combinations

Therapeutic combinations of the invention comprise, in addition to one or more antiepileptic agents, one or more psychostimulant agents effective in combination to provide enhanced treatment of one or more psychological disorders or symptoms or another underlying cause of the symptom(s) in comparison with either agent alone. The therapeutically effective amount of co-therapy comprising administration of one or more psychostimulant agents and at least one suitable anti-epileptic agent would be the amount of the psychostimulant agent(s) and the amount of the suitable anti-epileptic agent(s) that, when taken together or sequentially, have a combined effect that is therapeutically effective.

The amount of each agent per unit dosage of combination may encompass currently therapeutically effective amounts of each agent when administered separately. Thus, generally, and without limitation, the pharmaceutical compositions herein will contain, per unit dosage unit, (e.g., tablet, capsule, powder, injection, suppository, teaspoonful and the like) of from about 0.1-3000 mg of each active agent independently or any range therein. The dosages, however, may be varied depending upon the requirement of the patients, the severity of the condition being treated and the agents being employed. The use of either daily administration or post-periodic dosing may be employed.

In certain preferred embodiments of therapeutic combinations and combination formulations or dosage regimes, particularly those utilized in particular methods of the invention described herein, the dose administered of the mood stabilizer is sub-therapeutic with respect to mood stabilization, controlling seizures or mania. This means that the dose administered is below the dose range that would be administered to epileptics and individuals with bipolar disorders to achieve mood stabilization, control of seizures or control of mania, as appropriate. As mentioned above, the use of such sub-therapeutic dosages is advantageous for the treatments described herein.

Therapeutically effective dosage levels and dosage regimens for the anti-convulsant and anti-epileptic agents disclosed herein used in the treatment of mood disorders or epilepsy and related disorders may be readily determined by one of ordinary skill in the art. For example, therapeutic dosage amounts and regimens for pharmaceutical agents approved for sale are publicly available, for example as listed on packaging labels, in standard dosage guidelines, in standard dosage references such as the Physician's Desk Reference (Medical Economics Company or online at http://www.pdrel.com) and other sources.

In the case of sodium valproate, the product information for Epilim (Sanofi-Aventis) states that, for the treatment of mania (e.g. bipolar disorder) in adults, control of symptoms typically occurs within the range of 1,000 to 2,000 mg/day, (i.e. approximately 20 to 30 mg/kg/day). In the case of carbamazepine, a typical dose for treating epileptic seizures is in the range of from 400 to 800 mg/day. In the case of topiramate, the target dose for controlling epileptic seizures is between 100 to 500 mg/day.

By contrast, in relation to sodium valproate (and derivatives thereof), a sub-therapeutic dose with respect to mood stabilization is considered in this context to be less than 400 mg/day or 4 mg/kg/day, a preferred dose being less than 300 mg/day. The minimum dose is typically at least 25 mg/day, such as at least 50 or 100 mg/day, or at least 0.3, 0.5 or 1 mg/kg/day. The doses are expressed both independently of patient weight and based on patient weight since minimum and maximum doses can apply. Typically, the mg/kg/day is more commonly applied in relation to children whereas the total mg/day may be more appropriate for adults. These dosages in relation to sodium valproate and derivatives thereof represent, at the upper end, less than 50% of the lower end of the normal therapeutic dose range for treating epilepsy or bipolar disorder, and at the lower end, about 5 to 10% of the normal therapeutic dose range for treating epilepsy or bipolar disorder. These dosages can be used as a guide for calculating the relative dosages of other mood stabilizers that would constitute a sub-therapeutic dose.

For example, in the case of carbamazepine, a preferred sub-therapeutic dose is in the range of from 25 to 200 mg/day, such as more than 50, 75 or 100 mg/day but less than 250 200 or 150 mg/day. In the case of topiramate, a preferred sub-therapeutic dose is in the range of from 6.25 to 75 mg/day, such as at least 10, 15, 20, 30 or 40 mg/day but less than 80, 75 or 60 mg/day. In the case of phenytoin, a preferred sub-therapeutic dose is in the range of from 20 to 80 mg/day, such as more than 30 or 40 mg/day but less than 70 or 60 mg/day. In the case of pregabalin, a preferred sub-therapeutic dose is in the range of from 30 to 80 mg/day, such as more than 30 or 40 mg/day but less than 80 or 70 mg/day. In the case of rufinamide a preferred sub-therapeutic dose is in the range of from 5 to 200 mg/day, such as more than 10 or 20 mg/day but less than 150 or 175 mg/day.

Preferably, the sub-therapeutic dose is less than 50%, such as less than 40% or 30%, of the minimum dose that would be administered to epileptics and individuals with bipolar disorders to achieve mood stabilization, control of seizures or control of mania, as appropriate. For example the inventor has found that 10% of the normal minimum dose that would be administered to epileptics and individuals with bipolar disorders to achieve mood stabilization, control of seizures or control of mania, as appropriate, works well for the particular compounds tested in human subjects. The sub-therapeutic dose may be as little as 2.5%, 5% or 10% of the minimum dose that would be administered to epileptics and individuals with bipolar disorders to achieve mood stabilisation, control of seizures or control of mania, as appropriate.

The following is a list of some AED with their usual minimum anti-convulsant doses to illustrate a calculation of an initial sub-therapeutic AED dose. A sub-therapeutic dose for mood stabilization in the context of the present invention is therefore preferably (though not exclusively) less than 50%, such as less than 40% or 30% of the minimum dosages listed below for each particular agent e.g. for Ethotoin, a sub-therapeutic dose is less than 500 mg/day, such as less than 400 or 300 mg/day. The minimum dose to be administered in the context of the present invention is preferably at least 2.5, 5 or 10% of the minimum therapeutic dose for mood stabilization listed below, e.g. in the case of Ethotoin, at least 25, 50 or 100 mg/day. In the case of rufinamide, a preferred dose within the sub-therapeutic range for antiepileptic therapy or mood stabilization would be less than 50% of the minimum therapeutic dose for mood stabilization listed below, i.e. less than 200 mg/day.

| Agent | Minimum Dose/day effective for mood stabilisation or treatment of epileptic symptoms or events |
|---|---|
| Aminoglutethimide | 125 mg |
| Barbexaclone | 200 mg in divided doses |
| Belcamide | 1 mg |
| Brivaracetam | 100 mg |
| Carbamazepine | 400 mg |
| Clobazam | 5 mg/kg daily |
| Clonazepam | 1 mg |
| Ethadione | 1000 mg |
| Ethosuximide | 1000 mg |
| Ethotoin | 1000 mg |
| Felbamate | 1200 mg |
| Fosphenytoin Sodium | 10 mg/kg |
| Gabapentin | 900 mg |
| Lacosamide | 200 mg |
| Lamotrigine | 100 mg |

-continued

| Agent | Minimum Dose/day effective for mood stabilisation or treatment of epileptic symptoms or events |
|---|---|
| Levetiracetam | 1000 mg |
| Losigamone | 1500 mg |
| Mephenytoin | 200 mg |
| Methoin | 1000 mg |
| Methsuximide | 300 mg |
| Oxcarbazepine | 600 mg |
| Paramethadione | 300 mg |
| Perampanel | 2 mg |
| Phenacemide | 500 mg |
| Pheneturide | 600 mg |
| Phensuximide | 1000 mg |
| Phenytoin | 200 mg |
| Pregabalin | 300 mg |
| Primidone | 750 mg |
| Retigabine | 600 mg |
| Rufinamide | 400 mg |
| Sultiame | 200 mg |
| Tiagabine Hydrochloride | 30 mg |
| Topiramate | 100 mg |
| Trimethadione | 900 mg |
| Vigabatrin | 1000 mg |
| Zonisamide | 200 mg |

In some preferred embodiments, the dosage administered of AED mood stabiliser/anti-convulsant is sub-therapeutic for mood stabilization for the entire, or at least substantially the entire, treatment period. In other words, it is preferred that the dosage administered of mood stabiliser does not exceed the maximum stated sub-therapeutic dosages described above throughout the treatment.

Particularly preferred combinations of mood stabilizers and psychostimulants are: (i) one or more of sodium valproate and derivatives thereof, topiramate, carbamazepine, oxcarbazepine, phenytoin, gabapentin or pregabalin together with (ii) one or more of methylphenidate, amphetamines (e.g. dextroamphetamine), Lisdexamfetamine (L-lysine-d-amphetamine) or mixed amphetamine salts. For combination formulations comprising a mood stabilizer and a psychostimulant, the intended daily dose of mood stabilizer may range from 0.5 mg/d to less than 50% of the minimum dosages for treatment of epilepsy or mood disorder for each particular mood stabilizer, while the amount of psychostimulant provided may range from 0.5 to 250 mg/d intended daily dose.

Particular doses for particular combinations may be conceptually taken from a matrix formed by rows of AED doses with columns of psychostimulant doses. For example, an entry of (20 mg of AED, 30 mg of psychostimulant) in a matrix denotes 20 mg of AED and 30 mg of psychostimulant compounded as, for example, a single tablet or unit dose. Such a dose may be formulated or effective as a single, daily dose, or may be repeated a number of times in a day to result in a total daily dose of 80 mg of AED and 120 mg of psychostimulant. The units of measure of each agent may be divided as convenient into steps of 0.01, 0.5, 1.0, 2.0, 5.0 mg and the like. The units are not constrained by any particular step value and all possible values between the minimum and maximum doses for each agent are contemplated. Thus, the dimensions of the matrix row relevant to any particular AED are formed by its minimum and maximum contemplated doses along with the desired step values. Similarly, the matrix column dimensions are formed by the minimum and maximum contemplated doses of psychostimulants along with the desired step values. To include two or more AEDs or psychostimulants in a combination the matrix dimensions are increased by the addition of a dimension corresponding to the further agent. Hence, a 3 dimensional matrix would list all contemplated combination of three active agents. All combination unit doses and pharmaceutical compositions so described are within the scope of the invention.

The following exemplary embodiments are illustrative. As is understood by those of skill in the art, all formulations and unit dosages within the contemplated ranges of active agent combinations of the invention described herein are included in the scope of the invention. Particular amounts of each agent per unit dosage will be crafted to allow a frequency of administration or ingestion as appropriate to facilitate achieving the relevant effective daily dose in practice.

Exemplary embodiments provide sodium valproate (or a derivative thereof) in daily effective doses ranging from about 50 mg to 200 mg and methylphenidate in doses ranging from about 30 mg to 125 mg. In this particular embodiment the dose may be expressed on a per kilogram basis: sodium valproate (or derivative thereof) is given at from about 0.8 mg/kg/d to 3.4 mg/kg/d and methylphenidate from about 0.6 mg/kg/d to 1.7 mg/kg/d. The daily effective dose of this example may be achieved, for example, by compounding a pharmaceutical composition comprising from 12.5 mg to 50 mg sodium valproate (or a derivative thereof) and from 7.5 mg to 31.5 mg methylphenidate, which unit dose may be administered as needed to achieve the total desired daily dose, e.g. one, two, three, four or more times a day. More broadly, a pharmaceutical composition of this embodiment comprises from 1 mg to 400 mg sodium valproate (or a derivative thereof) and from 1 mg to 400 mg methylphenidate. Alternatively, and by way of a further non-limiting example, the daily dose may be provided as a trans-dermal patch comprising sodium valproate (or a derivative thereof) and methylphenidate such that the patch delivers in one day a total daily dose described herein.

Further exemplary embodiments provide sodium valproate (or a derivative thereof) in daily effective doses ranging from about 50 mg to 400 mg and dextroamphetamine sulphate in doses ranging from about 20 mg to 75 mg. In this particular embodiment the dose may be expressed on a per kilogram basis: sodium valproate (or derivative thereof) is given at from about 0.5 mg/kg/d to 5.7 mg/kg/d and methylphenidate from about 0.2 mg/kg/d to 1.1 mg/kg/d. An example of a pharmaceutical composition of this embodiment therefore comprises from 1 mg to 400 mg sodium valproate (or a derivative thereof) and from 1 to 75 mg dextroamphetamine sulphate.

Further exemplary embodiments provide sodium valproate (or a derivative thereof) in daily effective doses ranging from about 5 mg to 50 mg and dextroamphetamine sulphate in doses ranging from about 1 to 20 mg. In this particular embodiment the dose may be expressed on a per kilogram basis: sodium valproate (or derivative thereof) is given at from about 0.1 mg/kg/d to 0.7 mg/kg/d and dextroamphetamine sulphate from about 0.01 mg/kg/d to 0.3 mg/kg/d. An example of a pharmaceutical composition of this embodiment comprises from 1.25 mg to 12.5 mg sodium valproate (or a derivative thereof) and from 0.25 mg to 5 mg, which unit dose may be administered several times a day. More broadly, a pharmaceutical composition of this embodiment comprises from 0.1 mg to 50 mg sodium valproate (or a derivative thereof) and from 0.1 to 20 mg dextroamphetamine sulphate.

Still further exemplary embodiments provide sodium valproate (or a derivative thereof) in daily effective dose of about 120 mg and dextroamphetamine sulphate in daily effective does of about 40 mg. In this particular embodiment the dose may be expressed on a per kilogram basis: sodium valproate (or derivative thereof) is given at about 1.6 mg/kg/d and dextroamphetamine sulphate at about 0.5 mg/kg/. An exemplary unit dose of this example may be achieved by compounding a unit dose comprising about 30 mg sodium valproate (or a derivative thereof) and 10 mg dextroamphetamine sulphate, which unit dose may be administered several times a day. A further example of a pharmaceutical composition of this embodiment comprises about 120 mg of sodium valproate or derivative thereof and 40 mg of dextroamphetamine sulphate. More broadly, a pharmaceutical composition comprises from 1 mg to 400 mg sodium valproate (or a derivative thereof) and from 1 mg to 200 mg dextroamphetamine sulphate.

Further exemplary embodiments provide topiramate in daily effective doses ranging from about 1 mg to 80 mg and methylphenidate in daily effective doses ranging from about 1 mg to 400 mg. In this particular embodiment the dose may be expressed on a per kilogram basis: topiramate is given at from about 0.1 mg/kg/d to 1.1 mg/kg/d and methylphenidate from about 0.01 mg/kg/d to 5.5 mg/kg/d. An example of a pharmaceutical composition of this embodiment comprises from 0.25 mg to 12.5 mg topiramate and containing from 2.5 to 50 mg methylphenidate. More broadly, a pharmaceutical composition comprises from 0.5 mg to 80 mg topiramate and from 1 to 400 mg methylphenidate.

Further exemplary embodiments provide topiramate in daily effective doses ranging from about 1 mg to 80 mg and dextroamphetamine sulphate in daily effective doses ranging from about 1 mg to 200 mg. In this particular embodiment the dose may be expressed on a per kilogram basis: topiramate is given at from about 0.1 mg/kg/d to 1.1 mg/kg/d and dextroamphetamine sulphate from about 0.01 mg/kg/d to 2.85 mg/kg/d. An example of a pharmaceutical composition of this embodiment comprises from 0.25 mg to 12.5 mg topiramate and from 2.5 mg to 50 mg dextroamphetamine sulphate. More broadly, a pharmaceutical composition comprises from 0.5 mg to 80 mg topiramate and from 1 mg to 200 mg dextroamphetamine sulphate.

Yet further exemplary embodiments provide phenytoin in daily effective doses ranging from about 10 mg to 80 mg and methylphenidate in daily effective doses ranging from about 1 mg to 400 mg. In this particular embodiment the dose may be expressed on a per kilogram basis: phenytoin is given at from about 0.01 mg/kg/d to 1.1 mg/kg/d and methylphenidate from about 0.01 mg/kg/d to 5.5 mg/kg/d. Accordingly, the daily effective dose of this example may be achieved by compounding a pharmaceutical composition comprising 1, 2, 5, 10 or 12.5 mg to 60 mg phenytoin and from 2.5 to 50 mg methylphenidate, which tablet may be administered four times a day. More broadly, a pharmaceutical composition comprises from 1 mg to 100 mg phenytoin and from 1 mg to 400 mg methylphenidate.

Further exemplary embodiments provide phenytoin in daily effective doses ranging from about 10 mg to 80 mg and dextroamphetamine sulphate in daily effective doses ranging from about 1 mg to 200 mg. In this particular embodiment the dose may be expressed on a per kilogram basis: phenytoin is given at from about 0.01 mg/kg/d to 1.1 mg/kg/d and dextroamphetamine sulphate from about 0.1 mg/kg/d to 2.85 mg/kg/d. Accordingly, an exemplary pharmaceutical composition comprises from 12.5 mg to 60 mg phenytoin and from 2.5 mg to 50 mg dextroamphetamine sulphate. More broadly, a pharmaceutical composition comprises from 0.25 mg to 100 mg phenytoin and dextroamphetamine sulphate from 1 mg to 200 mg.

Additional exemplary embodiments provide rufinamide in daily effective doses ranging from about 1 mg to 200 mg and methylphenidate in daily effective doses ranging from about 1 mg to 400 mg. In this particular embodiment the dose may be expressed on a per kilogram basis: rufinamide is given at from about 0.01 mg/kg/d to 2.85 mg/kg/d and methylphenidate from about 0.1 mg/kg/d to 5.3 mg/kg/d. Accordingly, the daily effective dose of this example may be achieved by administering as needed a pharmaceutical composition comprising from 1 mg to 50 mg rufinamide and comprising from 2.5 to 50 mg methylphenidate. More broadly, a pharmaceutical composition comprises from 0.5 mg to 200 mg rufinamide and from 1 to 400 mg methylphenidate.

Still further exemplary embodiments provide rufinamide in daily effective doses ranging from about 1 mg to 200 mg and dextroamphetamine sulphate in daily effective doses ranging from about 1 mg to 200 mg. In this particular embodiment the doses may be expressed on a per kilogram basis: rufinamide is given at from about 0.01 mg/kg/d to 2.85 mg/kg/d and dextroamphetamine sulphate from about 0.1 mg/kg/d to 2.85 mg/kg/d. Accordingly, the daily effective dose of this example may be achieved by administering as needed a pharmaceutical composition comprising from 1 mg to 12.5 mg rufinamide and comprising from 2.5 mg to 50 mg dextroamphetamine sulphate. More broadly, a pharmaceutical composition comprises from 0.5 mg to 200 mg rufinamide and from 1 mg to 200 mg dextroamphetamine sulphate.

Additional exemplary embodiments provide sodium valproate in daily effective doses ranging from about 1 mg to 400 mg and Phenytoin in daily effective doses ranging from about 1 mg to 80 mg and dextroamphetamine sulphate in daily effective doses ranging from about 1 mg to 200 mg. In this particular embodiment the doses may be expressed on a per kilogram basis: valproate is given at from about 0.01 mg/kg/d to 5.5 mg/kg/d; Phenytoin is given at from about 0.1 mg/kg/d to 1 mg/kg/d; and dextroamphetamine sulphate from about 0.1 mg/kg/d to 2.85 mg/kg/d. Accordingly, the daily effective dose of this example may be achieved by administering as needed a pharmaceutical composition comprising from 1 mg to 100 mg sodium valproate (or a derivative thereof) and from 1 mg to 80 mg phenytoin and from 2.5 to 50 mg dextroamphetamine sulphate. More broadly, a pharmaceutical composition comprises from 1 mg to 400 mg sodium valproate (or a derivative thereof) and from about 1 mg to 100 mg Phenytoin and from 1 mg to 200 mg dextroamphetamine sulphate.

Still further exemplary embodiments provide sodium valproate in daily effective doses ranging from about 200 mg to 2000 mg and Phenytoin in daily effective doses ranging from about 1 mg to 80 mg and dextroamphetamine sulphate in daily effective doses ranging from about 1 mg to 200 mg. In this particular embodiment the doses may be expressed on a per kilogram basis: sodium valproate is given at from about 2.85 mg/kg/d to 28.5 mg/kg/d; Phenytoin is given at from about 0.1 mg/kg/d to 1.1 mg/kg/d; and dextroamphetamine sulphate from about 0.1 mg/kg/d to 2.85 mg/kg/d. For example, the daily effective dose of this example may be achieved by administering as needed a pharmaceutical composition comprising from 2.5 mg to 100 mg sodium valproate (or a derivative thereof) and from about 0.25 mg to 80 mg phenytoin and from 2.5 to 50 mg dextroamphetamine sulphate. More broadly, a pharmaceutical composition comprises from 1 mg to 2000 mg sodium valproate (or a derivative thereof) and from about 1 to 80 mg Phenytoin and from 1 mg to 200 mg dextroamphetamine sulphate.

Yet further exemplary embodiments provide sodium valproate in daily effective doses ranging from about 1 mg to 2000 mg and Topiramate in daily effective doses ranging from about 1 mg to 75 mg and dextroamphetamine sulphate in daily effective doses ranging from about 1 mg to 200 mg. In this particular embodiment the doses may be expressed on a per kilogram basis: valproate is given at from about 0.01 mg/kg/d to 25 mg/kg/d; Topiramate is given at from about 0.1 mg/kg/d to 1.1 mg/kg/d; and dextroamphetamine sulphate from about 0.1 mg/kg/d to 2.85 mg/kg/d. For example, the daily effective dose of this example may be achieved by administering as needed a pharmaceutical composition comprising from 1 mg to 100 mg sodium valproate (or a derivative thereof) and from 1 mg to 80 mg Topiramate and from 2.5 mg to 100 mg dextroamphetamine sulphate. More broadly, a pharmaceutical composition comprises from 1 mg to 2000 mg sodium valproate (or a derivative thereof) and from about 1 mg to 80 mg Topiramate and from 1 to 200 mg dextroamphetamine sulphate.

Still further exemplary embodiments provide sodium valproate in daily effective doses ranging from about 1 mg to 2000 mg and Phenytoin in daily effective doses ranging from about 1 mg to 80 mg and dextroamphetamine sulphate in daily effective doses ranging from about 1 mg to 200 mg. In this particular embodiment the doses may be expressed on a per kilogram basis: valproate is given at from about 0.01 mg/kg/d to 25 mg/kg/d; Phenytoin is given at from about 0.1 mg/kg/d to 1.1 mg/kg/d; and dextroamphetamine sulphate from about 0.01 mg/kg/d to 2.85 mg/kg/d. Accordingly, the daily effective dose of this example may be achieved by administering as needed a pharmaceutical composition comprising from 1 mg to 100 mg sodium valproate (or a derivative thereof) and from 1 mg to 80 mg Phenytoin and from 2.5 mg to 100 mg dextroamphetamine sulphate. More broadly, a pharmaceutical composition comprises from 1 mg to 2000 mg sodium valproate (or a derivative thereof) and from about 1 mg to 100 mg Phenytoin and from 1 to 200 mg dextroamphetamine sulphate.

Anti-Addictive Combinations

In certain embodiments, combinations of anti-epileptic agents and psychostimulants are provided that inherently and directly reduce the attractiveness of the psychostimulant agents for abuse or misuse or addiction. The presence of anti-epileptic agents in combination with psychostimulants directly reduces the ultimate attractiveness of this formulation for misuse. If excessive doses of the combination are taken, i.e. in amounts to deliver the "high" of the psychostimulant alone, the AED present in the combination would be at such a dose as to operate as a cerebral depressant thereby counteracting stimulating properties of the psychostimulant. This reduces the potential for diversion and misuse. The combinations therefore have a twofold advantage: the first as a cognitive enhancer the second as directly reducing the potential for abuse of this compound.

Additional Therapeutic Combinations

In certain alternative embodiments, patients receive a combination therapy of an AED, at a dose which is subtherapeutic for mood stabilization, and a non-stimulant treatment for ADHD. In a preferred embodiment, the non-stimulant is a noradrenaline (norepinephrine) or dopamine reuptake inhibitor, preferably Atomoxetine (3R)—N-methyl-3-(2-methylphenoxy)-3-phenyl-propan-1-amine), typically administered as the hydrochloride, Buprorion ((±)-2-(tert-butylamino)-1-(3-chlorophenyl)propan-1-one), Venlafaxin (1-[2-dimethylamino-1-(4-methoxyphenyl)-ethyl] cyclohexan-1-ol), or Devenlafaxin. Other examples include sibutramine, nefazodone, milnacipran, desipramine, duloxetine and bicifadine. For the avoidance of doubt, the non-stimulants can be applied to all embodiments that refer to combination therapy with anti-epileptic drugs and psychostimulants, the non-stimulants being administered or present in place of, or in addition to, said psychostimulants. Accordingly, a pharmaceutical composition of the invention comprises from 0.1 mg to 400 mg of mood stabiliser and from 0.1 mg to 1000 mg of non-stimulant as described above.

In certain further, and alternative embodiments, patients receive a combination therapy of a mood stabiliser, at a dose which is sub-therapeutic for mood stabilization and caffeine or nicotine in therapeutically effective amounts in combination. Accordingly, a pharmaceutical composition of the invention comprises from 0.1 mg to 400 mg of mood stabiliser and from 1 to 1000 mg caffeine or nicotine. In a particular combinations or therapeutic applications, the unit dose or pharmaceutical compositions comprises from 0.1 mg to 400 mg of mood stabilizer wherein the mood stabilizer is other than a gaba analog, gabapentin or pregabalin and from 1 mg to 1000 mg caffeine or nicotine. In certain, preferred combinations, the mood stabilizer in combination with caffeine or nicotine is selected from the group consisting of valproate, rufinamide, topiramate, and phenytoin.

Pharmaceutical Compositions

AEDs, alone or in combination with psychostimulants, may be administered in the form of a pharmaceutical composition, which further comprises a pharmaceutically acceptable carrier, diluent and/or excipient.

In a particular aspect, the invention provides a pharmaceutical composition comprising, in combination, one or a plurality of anti-epileptic agents, or a pharmaceutically acceptable salt thereof, and one or a plurality of psychostimulants, or pharmaceutically acceptable salt thereof.

In another particular aspect, the invention provides a pharmaceutical kit comprising a first pharmaceutical composition comprising (i) one or a plurality of anti-epileptic agents or a pharmaceutically acceptable salt thereof, together with a pharmaceutically acceptable carrier or diluent and (ii) a second pharmaceutical composition comprising one or a plurality of psychostimulants together with a pharmaceutically acceptable carrier, diluent or excipient.

Examples of routes of administration for which the pharmaceutical composition may be suitable include, but are not limited to, oral, intravenous (iv), intramuscular (im), subcutaneous (se), trans-dermal, and rectal. Compositions may also be administered directly to the nervous system including, but not limited to, intracerebral, intraventricular, intracerebroventricular, intrathecal, intracisternal, intraspinal or peri-spinal routes of administration by delivery via intracranial or intravertebral needles or catheters with or without pump devices. The psychostimulant(s) and the anticonvulsant or anti-epileptic agent(s) may be administered according to simultaneous or alternating regimens, at the same or different times during the course of the therapy, concurrently in divided or single forms.

Pharmaceutical compositions containing one or more of the agents described herein can be prepared by intimately mixing the compound or compounds with a pharmaceutical carrier, diluent and/or excipient according to conventional pharmaceutical compounding techniques.

As used herein, "pharmaceutically acceptable carrier" includes any material which, when combined with an active ingredient of a composition, allows the ingredient to retain biological activity and without causing disruptive reactions in the subject. Examples include, but are not limited to, any of the standard pharmaceutical carriers such as a phosphate buffered saline solution, water, emulsions such as oil and water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA).

The carrier may take a wide variety of forms depending upon the desired route of administration (e.g., oral, parenteral). Thus, for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

For use in medicine, the salts of the agents of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydrocy-ethanesulfonic acid, formic acid, fumaric acid, galactaric acid, gentisic acid, glucoheptonic acid, D-gluconic acid, D-glucoronic acid, L-glutamic acid, .alpha.-oxo-glutaric acid, glycolic acid, hipuric acid, hydrobromic acid, hydrochloric acid, (+)-L-lactic acid, (.+-.)-DL-lactic acid, lactobionic acid, maleic acid, (−)-L-malic acid, malonic acid, (.+-.)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Optionally, the oral solid dosage form includes a sustained release carrier that effectuates the sustained release of the AED, or both the AED and the psychostimulant when the dosage form contacts gastrointestinal fluid. The sustained release dosage form may comprise a multiplicity of substrates and carriers that include the agents. The substrates may comprise matrix spheroids or may comprise inert pharmaceutically acceptable beads that are coated with the agents. The coated beads are then preferably overcoated with a sustained release coating comprising the sustained release carrier. The matrix spheroid may include the sustained release carrier in the matrix itself, or the matrix may comprise a simple disintegrating or prompt release matrix containing the drugs, the matrix having a coating applied thereon which comprises the sustained release carrier. In yet other embodiments, the oral solid dosage form comprises a tablet core containing the agents within a normal or prompt release matrix with the tablet core being coated with a sustained release coating comprising the sustained release carrier. In yet further embodiments; the tablet contains the agents within a sustained release matrix comprising the sustained release carrier. In yet further embodiments, the tablet contains the AED within a sustained release matrix, and the Psychostimulant coated into the tablet as an immediate release layer.

In some embodiments of the invention, the pharmaceutical compositions containing the psychostimulant and AED agents set forth herein are administered orally. Such oral dosage forms may contain one or all of the agents in immediate or sustained release form. The oral dosage forms may be in the form of tablets, troches, lozenges, aqueous, solid or semi-solid solutions or mixtures, or oily suspensions or solutions, dispersible powders or granules, emulsions, multiparticulate formulations, syrups, elixirs, and the like.

In other embodiments, a pharmaceutical composition containing the AED(s) and psychostimulant(s) can be administered in dosage form as a topical preparation, a solid state and or depot type transdermal delivery device(s), a suppository, a buccal tablet, sub-lingual preparation, or an inhalation formulation such as a controlled release particle formulation or spray, mist or other topical vehicle, intended to be inhaled or instilled into the sinuses.

The pharmaceutical compositions containing the agents set forth herein may alternatively be in the form of microparticles such as microcapsules, microspheres and the like, which may be injected or implanted into a human patient, or other implantable dosage forms known to those skilled in the art of pharmaceutical formulation.

For administration orally, the compounds may be formulated individually or in combination as sustained release preparations. If formulated individually, different release times or bioavailability may be afforded each active agent though they may ultimately be compounded or mixed together into one unit dose. Numerous examples of techniques for formulating sustained release preparations are described in the following references: U.S. Pat. Nos. 4,891,223; 6,004,582; 5,397,574; 5,419,917; 5,458,005; 5,458,887; 5,458,888; 5,472,708; 6,106,862; 6,103,263; 6,099,862; 6,099,859; 6,096,340; 6,077,541; 5,916,595; 5,837,379; 5,834,023; 5,885,616; 5,456,921; 5,603,956; 5,512,297; 5,399,362; 5,399,359; 5,399,358; 5,725,883; 5,773,025; 6,110,498; 5,952,004; 5,912,013; 5,897,876; 5,824,638; 5,464,633; 5,422,123; and 4,839,177; WO 98/47491; and U.S. Patent Application Publications 2005/0266078; 2008/0057123; 2008/0026070; 2008/00757769; and 2008/0031946, all of which are incorporated herein by reference.

As an example of how certain embodiments of the pharmaceutical compositions of this invention are prepared, one or more of the psychostimulant agents and one or more of the anticonvulsant or anti-epileptic agents are intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredients necessary to deliver an effective dose as described herein.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above.

In the context of combination unit doses, a pharmaceutical composition comprising the active agents may be formulated with distinct halves or further subdivisions, each half or subdivision comprising primarily one agent. Scoring or pre-division of the halves or subdivisions thereby allow easy modulation of dose of each active agent.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. In an additional embodiment, one or more of the psychostimulant agents may be separately formulated or compounded, then coated or embedded in one or more of the anticonvulsant or anti-epileptic agents or formulations thereof. Alternatively, the anticonvulsant or anti-epileptic agents or formulations thereof may be embedded in or otherwise bound to psychostimulant agents or their formulations. Thus, the two or more active agents may be compounded separately but ultimately provided together in one unit dose as a combination. Each, separately compounded agent may thus be provided in timed release, slow release, or other suitable formulation specifically advantageous to that agent, though ultimately provided as a single unit dose.

Methods of Treatment of Psychiatric Disorders

It will be generally understood that therapeutic methods may be practiced preventatively to prophylactically treat a psychiatric disorder, or may be used to treat an existing, recurring or on-going psychiatric disorder. Prophylactic treatments may be appropriate where, for example, a subject has a genetic predisposition and/or family history of a psychiatric disorder.

In this regard, methods may further include, prior to administration of the anti-epileptic agent alone or in combination with the psychostimulant, determining whether said subject is, or may be, in need of prophylactic or therapeutic treatment for said psychiatric disorder. This step may be performed by clinical assessment, genetic testing or genetic counseling, alone or in combination.

Preferably, patients, subjects or individuals treated by the method may be adult, juvenile, adolescent, child or infant humans.

In one embodiment, the psychiatric disorder is associated with an impairment or deficiency in higher order executive functioning. The executive system is a theorized cognitive system in psychology that controls and manages other cognitive processes. It is also referred to as the executive function, supervisory attentional system, or cognitive control.

The concept is used by psychologists and neuroscientists to describe a loosely defined collection of brain processes which are responsible for planning, cognitive flexibility, abstract thinking, rule acquisition, initiating appropriate actions and inhibiting inappropriate actions, and selecting relevant sensory information.

Higher order executive functioning is thought to be heavily involved in handling novel situations outside the domain of some of our 'automatic' psychological processes that could be explained by the reproduction of learned schemas or set behaviors. Psychologists have outlined five types of situation where routine activation of behavior would not be sufficient for optimal performance: (i) those that involve planning or decision making; (ii) those that involve error correction or troubleshooting; (iii) situations where responses are not well-learned or contain novel sequences of actions; (iv) dangerous or technically difficult situations; and/or (v) situations which require the overcoming of a strong habitual response or resisting temptation.

In another embodiment, the psychiatric disorder is not a developmental disorder or a disorder usually diagnosed in infancy, childhood or adolescences In yet another embodiment, the psychiatric disorder is a degenerative disorder. Examples of degenerative disorders include Mild Cognitive Impairment (MCI), Alzheimer's Disease, Amyotrophic Lateral Sclerosis, Corticobasal Degeneration, Creutzfeldt-Jakob Disease, Dementia with Lewy Bodies, Frontotemporal Dementia, Huntington's Disease, Progressive Supranuclear Palsy, Vascular Dementia, movement disorders such as Parkinson's disease, dementia associated with multiple sclerosis and motor neurone disease.

In still yet another embodiment, the psychiatric disorder is a psychotic disorder. Non-limiting examples are schizophrenia and psychotic disorders and/or behaviour resulting from causes including brain tumors, drug abuse with amphetamines, cocaine, cannabis, alcohol etc., brain damage, bipolar disorder (manic depression), severe clinical depression, severe psychosocial stress, sleep deprivation, some focal epileptic disorders especially if the temporal lobe is affected, exposure to some traumatic event (e.g. violent death, road accident), abrupt or over-rapid withdrawal from certain recreational or prescribed drugs, neurological disorders, including: brain tumour, dementia with Lewy bodies, multiple sclerosis, sarcoidosis, Alzheimer's Disease and Parkinson's Disease.

In still yet another embodiment, the psychiatric disorder is associated with reduced adherence, or non-compliance, with a medication regime that includes the administration of a therapeutic agent other than, or in addition to, a psychostimulant. This embodiment in particular relates to long-time, multiple or complex medication regimes, such as those used in the treatment of hypertension, elevated cholesterol/lipids and diabetes (e.g insulin therapy). For example, compliance with long-term treatment for chronic asymptomatic conditions such as hypertension is in the order of only 50% (Loghman-Adham 2003).

In a further embodiment, the psychiatric disorder is an eating disorder. Non-limiting examples include Anorexia Nervosa and Bulimia Nervosa.

AED Therapy

One particular aspect of the invention provides a method of treating a psychiatric disorder other than epilepsy, bipolar disorder or attention deficit hyperactivity disorder (ADHD), a communication disorder, a pervasive development disorder or an anxiety disorder, in a subject in need thereof, including the step of administering to the subject an anti-epileptic agent, or a pharmaceutically acceptable salt thereof, to thereby treat the psychiatric disorder, wherein the amount of anti-epileptic agent is sub-therapeutic for mood stabilization treatment of epilepsy or epileptic symptoms.

Another particular aspect of the invention provides an anti-epileptic agent, or a pharmaceutically acceptable salt thereof, for use in treating a psychiatric disorder other than epilepsy, attention deficit hyperactivity disorder (ADHD), a communication disorder, a pervasive development disorder and/or an anxiety disorder.

It will be appreciated that more than one AED may be administered according to these aspects.

In particular embodiments, treatment of psychotic disorders such as schizophrenia (particular early intervention) and reduced adherence, or non-compliance, with a medication regime are particularly suited to single AED therapy without a psychostimulant.

In other particular embodiments, treatment of dementia and sleep disorders are particularly suited to AED therapy without a psychostimulant, wherein two or more different AEDs are administered.

Co-Therapy with AEDs and Psychostimulants

In yet another particular aspect, the invention provides a method of treating a psychiatric disorder other than epilepsy, bipolar disorder or attention deficit hyperactivity disorder (ADHD), in a subject in need thereof, including the step of administering to the subject an anti-epileptic agent, or a pharmaceutically acceptable salt thereof, and a psychostimulant, or pharmaceutically acceptable salt thereof, to thereby treat the psychiatric disorder, wherein the amount of anti-epileptic agent is sub-therapeutic for mood stabilization treatment of epilepsy or epileptic symptoms.

In still yet another particular aspect, the invention provides an anti-epileptic agent, or a pharmaceutically acceptable salt thereof, and a psychostimulant, or pharmaceutically acceptable salt thereof, in combination for use in treating a psychiatric disorder other than epilepsy, bipolar disorder or attention deficit hyperactivity disorder (ADHD).

In preferred embodiments, combination therapy is particularly suited to treating a psychiatric disorder selected from the group consisting of: degenerative disorders and/or movement disorders such as Parkinson's disease, dementia and Mild Cognitive Impairment addiction; reduced adherence; eating disorders such as Anorexia Nervosa and Bulimia Nervosa; and personality disorders.

In other particular embodiments of combination therapy, the psychiatric disorder is selected from the group consisting of: Communication Disorders; Pervasive Development Disorders; and Anxiety Disorders.

Particular, non-limiting examples of these embodiments include psychiatric disorders that fall within the DSM-IV-TR classification: Communication Disorders (e.g. Expressive Language Disorder, Mixed Receptive-Expressive Language Disorder, Phonological Disorder, Stuttering, Communication Disorder NOS (=Not Otherwise Specified); Pervasive Development Disorders (Autistic Spectrum Disorders such as Autistic Disorder and Asperger's Disorder; Rett's Disorder, Childhood Disintegrative Disorder and Pervasive Developmental Disorder NOS); and Anxiety Disorders (e.g. Generalized Anxiety Disorder).

In particular embodiments, one or a plurality of AEDs alone, or AEDs in combination with psychostimulants, may be administered in the form of a pharmaceutical composition, including but not limited to the particular pharmaceutical compositions hereinbefore described.

In view of the teachings of the invention, optimal dosages and schedules to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages. Where a subject or patient proves to be particularly sensitive to an agent or combination therapy, doses can be appropriately adjusted, or alternative choice of agent(s) made within the teaching of the invention.

One skilled in the art will recognize that a therapeutically effective dosage of the combinations of the present invention can include repeated doses within a prolonged treatment regimen that will yield clinically significant results. Advantageously, combinations of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen. The combinations may be administered through a single transdermal patch, or via subdivided transdermal patches or even separate transdermal patches, as may be desired.

Determination of effective dosages is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models. Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

So that the invention may be readily understood and put into practical effects, reference is made to the following non-limiting examples.

EXAMPLES

Introduction

The present invention has arisen, at least partly, from the inventor's clinical observations regarding a triad of presenting co-morbidities associated with abnormal or deficient cognitive processing, namely abnormal social processing, non-verbal learning disorders, and eye movement dysfunction. A general clinical observation is that in administering an anti-epileptic agent at low dose, alone or in combination with a psychostimulant, to individuals diagnosed with a variety of psychological disorders, the inventor has been able to achieve improved results on a task of rapid automatic naming (as tested by the Developmental Eye Movement Test). This correlates with both integrative, automatic processing as well as ocular movements, both of which require a higher executive control system. Similar benefits have been noted using the Alzheimer's Quick Test: AQT. An Assessment of Parietal Lobe Function has been used to screen and assess cognitive dysfunctions such as mild cognitive impairments of unspecified origins, dementias of the Alzheimer's type and dementias with Lewy bodies. Findings suggest that AQT may be used to identify early cognitive impairments, follow the progression of disease processes and monitor the effects of medication. The Paced Auditory Serial Addition Test (Gronwall, 1977) has also been used to assess improvement. It is commonly used as a neuropsychological measure of vigilance or sustained attention (Lezak, 1995); however, recent studies have indicated that PASAT performance is also related to divided attention, memory, information processing speed, and mathematical ability (Sherman, Strauss, and Spellacy, 1997; Brittain, LaMarche, Reeder, Roth, and Boll, 1991; Lezak, 1995; Roman, Edwall, Buchanan, and Patton, 1991).

Further, the inventor has demonstrated, and replicated in the clinical population, improvements in rapid automatic naming which correlate with a greater automaticity in reading (less effortful), both silently and out loud, together with enhanced verbal word finding ability. The improvements we have clinically observed and which have been subjectively described by individuals treated with the low dose anti-epileptic agents appear to be associated with both the improved efficiency of rapid automatic naming and ocular motor function. An individual's cognitive processes, with the concomitant higher executive functions to selectively attend, filter, integrate, reflect and prioritise thoughts and ideas, are underlined by the same system which is enhanced by the administration of low dose anti-epileptic agents, alone or in combination with a psychostimulant, and reflected in improved measures of eye movement function. The inventor observed enhancements in cognitive processing and higher executive functioning by measuring outcomes directly and indirectly associated with the enhancement of eye movement function.

Research and clinical observations have demonstrated that the usual dose of many anti-epileptic agents leads to behavioural change. It is clinically understood that this occurs through the anti-epileptic agents targeted action as a cerebral depressant, which results in a general cognitive impairment. This is in contrast to an enhancement of higher executive functioning, which we have noted at a low dose administration of anti-epileptic agents. Without wishing to be bound by theory, it is postulated that in low doses, the action of these medications is to enhance the afferent organisation, integration and prioritisation of information whereas, the action at the much higher (and usual) doses appears additionally act to suppress the efferent system.

The ability to organise, integrate and prioritise information; be it external, such as auditory, visual, tactile, olfactory; or internal, such as memories of past events thoughts and ideas in an effortless and almost unconscious manner, allows an individual to focus their attention on the content of a social interaction or conversation, rather than the mechanics. The underlying principle of the invention is that the cognitive processes involved in the organisation, integration and prioritisation of such information is primarily potentiated or enhanced by the use of low dose anti-epileptic drug. This beneficial and previously undescribed outcome has multiple applications both in the treatment and possible prevention of abnormal psychopathology and for normal psychological functioning.

The examples provided herein demonstrate the benefits of the invention and are presented as an indicator of the possible breadth of the impact on pharmacotherapy that using low dose levels of anti-epileptic drug may have, alone or in combination with psychostimulants. This is distinct from previous understandings of the action of these medications at higher doses, which is dependant on their generally accepted action as cerebral depressants. It is further noted that the actions of each of the various anti-epileptic agents are similar but not identical, and appear to have an enhanced synergistic action when they are also combined at low dose and in combination with psychostimulants. Moreover, the range of conditions amenable to treatment by low doses of AEDs is substantially widened by the therapeutic combination of psychostimulants with low doses of AEDs.

At high dose levels of anti-epileptic drug, impulsivity is reduced by the general slowing of cognitive functioning. This has been a useful and desired therapeutic effect in many conditions. However, this sense of cognitive depression and slowing is unpopular with those taking the medication. Individuals report a reduction in the ability to think clearly and organise thoughts and actions. In contrast, at significantly lower dose levels of the same medications, organisation and clarity of thoughts is actually enhanced and the therapeutic effects of psychostimulants potentiated. This leads to an improvement in re-ordering and prioritising of incoming information which, in turn, leads to more effective, efficient and appropriate decision making. Instead of the individual feeling out of control as a consequence of slowed thinking, it is postulated that the individual is more able to correctly evaluate options and choose a more appropriate action. The individual often reports the ability to evaluate the choices available in a more logical and could be understood as a verbal process whereas previously they have made the same choices based on an impulsive, intuitive and fundamentally non logical process. At the end of which they have been unable to either understand themselves or explain to others the choices. That they felt it was the correct choice even though they would have difficulty later explaining it logically it simply appeared to represent a good idea at the time. This rapid and possible reflexive process is vital for many simple decisions we need to make in our life, particularly those which affect safety and similar more primitive evolutionary functions. However, it is less well adapted to the application in the more complex relationship and social functioning. This enhancement of the logical decision making process results in a reduction in impulsivity through a separate mechanism that would not be anticipated from previous clinical understanding of these medications as cerebral depressants.

It must also be noted that as a result of these positive outcomes, individuals are more motivated to take medication and therefore improved compliance rates result. At the usual higher doses, despite some effectiveness by an anti-epileptic agent's action as a general cerebral depressant, the acceptance by those taking them has been less as the medications are perceived to directly reduce the individual's ability to maintain autonomy. The decision-making process, which is already impaired as a consequence of the underlying condition, is further depressed by the therapeutic action of the anti-epileptic agents. We believe that such features are due to the inability to effectively, efficiently and concurrently evaluate multiple streams of incoming and outgoing information, which results in poor decision making, whereby the individual randomly and impulsively makes a decision or choice of action. We believe that use of AEDs at low dose levels will have an entirely different therapeutic effect, addressing features such as procrastination and 'not being able to think clearly'.

It is proposed that the present invention enhances decision making by allowing multiple choices to be considered in a flexible manner. The information which has been organised and integrated better through the action of the low dose anti-epileptic agents can be reviewed, compared, evaluated, ranked and finally prioritised, with efficiency and effectiveness. The converse is often noted in these patient groups. The greater the effort required to focus on a task often leads to a narrower range of attention, tunnel visioned or hyperfocused, in turn resulting in inflexibility Because the information relating to the decision and each option has been better organised, it also allows for learning to take place as the reasoning behind the decision is understood and most importantly, is available for future reference when similar demands are made. The logical approach enables the information to be later retrieved with less effort, a more efficient method that the more unique storage required when the decisions are non logical. This potential improvement in future functioning and efficiency that occurs when better choices are made, does not occur when the cognitive system is being depressed. As a result, the use of anti-epileptic agents at previous high therapeutic dose levels does not improve long-term learning as many beneficial, learned outcomes are not organised and integrated. As a result, the repeated presentation of similar situations is dealt with in a random manner, as occurred in the first encounter with the situation. The need to learn from past experiences is as vital as the ability to acquire and sustain mature social and intimate relationships. Our clinical experience with the therapeutic use of anti-epileptic agents at lower dose levels is in direct contrast to this outcome. Under treatment with lower doses of AEDs, learned and more adaptive behaviour becomes increasingly automated through better organisation and integration of information, requiring less conscious attention for them to be retrieved, and so the benefits have been maintained in the long-term at the same if not enhanced efficacy. This latter outcome has been reported by many individuals in our clinic, who over time have been able to further reduce the levels of their medications, while maintaining or continuing to improve their overall functioning.

We believe that this intervention of a low dose anti-epileptic agent, alone or in combination with a psychostimulant, will have applications in addition to the ones described below in areas that have been traditionally characterised by poor impulse control such as addiction, Obsessive-Compulsive Disorder, tics and other associated conditions.

Clinically we have noted a trend towards even lower doses of sodium valproate being more effective in younger age groups without acute episodes of diagnosable psychiatric illness. In these individuals there appears to be a greater sensitivity to the therapeutic benefits of sodium valproate. The dose range in these individuals is usually between 12.5-150 mg/day. (Above this dose the affect of the anti-epileptic drug is often associated with excessive slowing thought processes as described above). These individuals often describe uncontrolled and distressing thoughts. They report these intrusive thoughts as becoming more troublesome and harder to control with increasing age. The associated impairment also becomes more disabling, as the irrelevant and distressing thoughts occur both during and between episodes of illness. Despite stabilisation of their mood disorder, many of these individuals report continuing difficulties controlling the intrusive thoughts. The intensity of the thoughts and their associated distractibility results in increased difficulty sustaining social interactions. As a consequence these individuals become increasingly socially awkward and inexperienced. Although they may not always deteriorate in their ability to maintain social connectedness they do not keep pace with their peer group. As a result, they may be seen as immature and so important social supports are lost, which would otherwise help to stabilise and maintain the individuals' mental health. It is important to note that most of the individuals we have observed and treated in the clinic have neither a personal nor family history of a bipolar disorder or epilepsy.

On an appropriate dose of anti-epileptic agents, there would be a slowing or controlling of these thoughts, enabling robust improvement in the effortless ability to maintain social interaction. It is proposed that this ability is possibly the best prognostic indicator of future positive outcomes. In individuals requiring a high dose level of sodium valproate, we have clinically noted that the addition of an alternate low dose anti-epileptic drug further enhances the therapeutic gains, particularly in the ease of being able to maintain egocentric eye gaze. In such individuals, the dose of be sodium valproate may subsequently be reduced without a subsequent loss of therapeutic efficacy. We have further noted that in successfully treated individuals, over a period of stability in excess of six to twelve months that the dose of the sodium valproate can be successfully reduced even further without loss of efficacy. The changes observed and reported by the individuals appear to be reflected in improvements in oculo-motor functioning as measured with the developmental eye movement test.

In children and adolescents, stimulants can provide robust improvement in ADHD behavioural symptoms. However despite this, individuals often continue to experience functional impairment. In adults this is particularly evident in the area, often referred to as higher executive function. Higher executive function includes the processes involved in sequencing, organising and integrating information and sensory stimuli. It appears to be used during complex interpersonal interactions, which form the basis of human social communication. A communicative partner quickly detects impairments or breakdown in this area, although it may not be readily identified or described. The use of stimulant medication reduces the effort that is required to successfully complete a task. However, stimulants don't appear to act in a manner, which would allow the task to become easier and automatic for the individual, as would be predicted with repeated practice and exposure. As a result, fatigue is inevitable and is not counterbalanced by continued improvement and efficiency in the task, and eventually the task is ceased.

The same model can be applied to social interaction, for both individuals with or without ADHD. The benefit of psycho-stimulants appears to be related to their ability to reduce the effort required to undertake tasks. This effect is not limited to individuals with a DSM IV diagnosis of ADHD. It is a spectrum disorder and individuals without the full syndromal ADHD may benefit from treatment with a psycho-stimulant. In our experience, individuals with a clinical presentation of ADHD often present with impairments of social functioning that will respond to treatment with low dose anti-epileptic agents. We have observed individuals in the clinic, without symptoms consistent with a diagnosis of ADHD or who present with a subthreshold ADHD, but who respond well to a combination of appropriate doses of psychostimulant agents and low doses of anti-epileptic agents. Individuals report that doses above these levels tend to produce unacceptable side-effects. However, on a combination of psycho-stimulant plus a low dose anti-epileptic drug, individuals often experience a synergistic enhancement resulting from the combined outcomes of both medications. Further there are many individuals with co-morbid conditions who have impairment in both effortful attention and in cognitive functioning—organising, sequencing, integrating and prioritising information and sensory stimuli—who benefit from a reduction in the effort required to attend to a task as well as to sequence and organise thoughts. This benefit is provided by the combination of medications—low dose anti-epileptic agents plus psycho-stimulants.

We have noted that the tendency to hyper-focus on a specific topic during conversation does not reduce consistently or sufficiently when treated by stimulants alone. It is postulated that the individual can't process simultaneously the multiple streams of thought and sensory stimuli that usually occurs in normal social interaction. Instead, the individual chooses a familiar topic, which is considered 'safer or less demanding' and which demands less attention and effort. The individual may also resist following the natural flow of the conversation, rigidly sticking to their preferred topic. As a result, the communicative partner may perceive the individual as being awkward or tense during the social interaction. So although sufficient motivation and attention may be provided by the stimulant for conversation to occur, the task still requires considerable effort.

Another strategy commonly employed by individuals is to dominate the conversation. Normally, communicative partners would share the speaker and listener roles, each contributing actively to the social discourse, or conversation. However, these individuals may find it easier to simply take all the speaking turns, as allowing the other person to have their turn would mean that the individual might have to re-organise, integrate and re-prioritise the new information in order to respond appropriately. Again, the communicative partner is left feeling snubbed, as if their ideas and thoughts are not of interest. Inevitably, the individual will fatigue and simply drop out of the conversation, due to the effort involved.

Fatigue results in a similar though sometimes delayed experience of mental exhaustion and a sense of being unable to sustain attention, a state that existed prior to the commencement of stimulants. We have found that, unless there is an improvement in the ability to organise, integrate and prioritise information and sensory stimuli, the improved motivation provided by the stimulant will inevitably wane. This is seen in clinical situations with adults who have a diagnosis of ADHD, and who are treated with stimulant medication alone. The initial and at times miraculous improvement frequently gives way to an increasing disorganisation, non-adherence to medication and the eventual cessation of treatment. This highlights the need for an improved treatment method for ADHD that improvement is insufficient and full remission of symptoms should be the goal of therapy. It is postulated that an improved treatment methodology would target the impairment in the underlying cognitive functions of organisation, integration and prioritisation of information and sensory stimuli, as reported in individuals with ADHD.

Accordingly, Examples are provided herein which describe improved compositions for combination therapy of ADHD, comprising one or a plurality of AEDs with a psychostimulant.

Further examples are provided which demonstrate therapy of psychiatric disorders other than ADHD, which include administration of one or a plurality of AEDs and one or a plurality of psychostimulants.

Example 1—Treatment of Adult ADHD Sufferers with a Combination of Psychostimulant and Mood Stabiliser: Dexamphetamine and Valproate In the clinical setting a number of adults with ADHD experienced a combination therapy of stimulant medication (dexamphetamine) in combination with sodium valproate (VPA). The initial dosages used were from 15 to 70 mg/day of dexamphetamine and from 100 to 700 mg/day of VPA (Epilim) (=approximately 2 to 10 mg/kg/day). The Epilim product information supplied by Sanofi-Aventis for the treatment of mania (e.g. bipolar disorder) in adults suggests that control of symptoms occurs within the range of 1,000 to 2,000 mg/day, (i.e. 20 to 30 mg/kg/day). The dosages used in this trial were therefore substantially lower than the dosages required for treating mania.

The determination of the dose for the dexamphetamine was undertaken in a clinical sensitive open label manner. The dose was titrated upwards dependent on the clinical response and the freedom from side-effects. The dose range was between 15 and 70 mg a day. The frequency of the dosing also varied dependent upon the clinical response. The usual dose interval was between two to four hours. This dosing adjustment took place prior to the commencement of the sodium valproate. The sodium valproate medication was initiated once a day at 50 mg tablet or elixir and titrated upwards dependent on response, but not more than one increase every three days. The dose was given as a once or twice a day regime. During the titration phase, if clinically possible, no other adjustments to the pharmacotherapy were undertaken.

Following the initial results, the dosages for those patients on the higher dosages of sodium valproate (i.e. 500 or 700 mg) were re-titrated because such patients frequently experienced general cognitive and a resultant loss of efficacy.

The dosages of sodium valproate, after adjustment, varied between 50 mg/day, 100 mg/day, 150 mg/day or 200 mg/day (number of patients—120), with the majority of patients receiving between 50 to 150 mg/day with 300 mg/day usually the maximum. The data has demonstrated an effective dose of 40 mg of Dexamphetamine with a dosage of 120 mg of Sodium Valproate. With an average weight of 75.7 kg, the results equate with an average dose per kilogram per day of about 0.6 mg/kg Dexamphetamine and about 1.75 mg/kg Valproate.

Maximum, minimum, average and median dosages used are:

|  | Dexamphetamine | | Valproate | |
| --- | --- | --- | --- | --- |
|  | mg/d | mg/kg/d | mg/d | mg/kg/d |
| Average | 41.1842 | 0.5624 | 160.53 | 2.12 |
| Median | 40.0000 | 0.5814 | 100.00 | 1.32 |
| minimum | 20 | 0.2222 | 50.00 | 0.66 |
| maximum | 75 | 1.0638 | 300.00 | 3.96 |

This example shows a ratio of 1:3 using the median dosings of Dexamphetamine (0.58 mg/kg/d) and Sodium Valproate (1.32 mg/kg/d). Where patients appeared to be very sensitive to the medication, the dosing for this group was adjusted to 0.22 mg/kg/d Dexamphetamine with a Valproate dosing about 0.6 mg/kg/d.

Clinical assessments indicated that, under combination therapy of AED (Valproate) and psychostimulant (Dexamphetamine), patients often described their thoughts as slowing to a rate that was more manageable and less chaotic. This seemed to allow for more temporal sequencing of ideas, with a resulting overall improvement in psychosocial functioning. A large number of these patients had no evidence to suggest a personal or family history of a bipolar disorder. These patients benefited from a dose of AED below a typical initiation dose recommended for bipolar disorder, and significantly below the dose typically required to achieve control of symptoms of mania (i.e., achieve mood stabilization).

The results were assessed using the Conners Adult ADHD Rating scales completed by the patient and observer (usually partner or parent). In a sample of 26 patients who completed self CAARS rating scales at; pre treatment, stable on stimulant and stable on anti-epileptic drug (AED). 6 Of the 8 CAARS subscales showed significant quadratic improvement of at least p<0.5 after the addition of their AED to their stimulant therapy. With CAARS ADHD symptoms subscale the quadratic significance reached p<0.001. Robust improvement was similarly noted on the Quality of Life Scales.

A visual analogue scale which was used to compare the subjective benefit of addition of their AED to their initial experience of commencing stimulants showed that the two interventions were of similar benefit. This is significant in the context of the well reported robust treatment effect achieved on initiation of stimulants. The clinical reviews were consistent with the above findings.

A significant number of patients who reported a subjective improvement in ADHD symptoms also described an improvement in their reading and verbal comprehension abilities. They were more able to attend to the content of both the text and conversation, which was in direct contrast to their previously frustrating experiences of needing to put most of their mental effort into either reading or listening with relatively little comprehension occurring.

Additionally, the self-reported improvement appeared to correlate closely to notable changes in the complex interpersonal interaction during the clinical consultation. Verbal interactions between the treating psychiatrist and patients appeared more spontaneous and fluid, and patients appeared to be able to provide a higher level of subtle non-verbal feedback during conversations. It would appear, based on this appropriate non-verbal behaviour, that patients were experiencing a greater understanding of the content of the conversation. Patients also reported that reading seemed to require less effort, resulting in greater enjoyment in a task that had previously been very cognitively demanding. This clinical observation would appear to be consistent with the hypothesis by Samuelsson et al. (2004) that ADHD symptoms were more associated with impaired reading comprehension than with word decoding. The improvement as described by patients occurred almost immediately on initiation of therapy, prior to the opportunity for any additional learning to take place. Further, this would seem to preclude the acquisition of further decoding ability as a possible explanation for this improvement.

During the initial trials higher doses in excess of 400 mg Sodium Valproate were routinely used for some patients (VPA being relatively well tolerated). However doses above this level frequently led to general cognitive slowing and the resultant loss of efficacy. The patients often ceased the medication as a consequence of this and it was only on later re-challenge with a lower dose with a much slower re-titration that the ideal and more efficacious dose was identified.

From these observations it has been demonstrated that AEDs have a synergistic effect with psychostimulant medication at a dose of AED that would be considered sub-therapeutic if used only for mood stabilization. This novel use of AEDs has the potential to further enhance the understanding and improve the treatment outcome of those diagnosed and treated with stimulants for ADHD and related disorders.

Clinical example of a 53-year-old single man with a history of depression, alcohol dependence ADHD and social withdrawal. After commencement of Psycho stimulants noted a reduction in many of his symptoms although continued to use alcohol to slow his thoughts. After commencement of a low dose of sodium valproate noted he was able to organise and sequence his thoughts. He found conversations less effortful and was noted during the consultation to have an improvement in his egocentric gaze and improved cognition. This has been validated with the use of face tracking technology. He found his reading was less effortful with a better comprehension than he had ever experienced. He described a 50% improvement in his ability to study on commencement of the sodium valproate in addition to his psycho stimulant a similar magnitude as to his perception of improvement on the commencement of psycho stimulants. These improvements were initially noted on a dose of 50 mg of sodium valproate and his improvement was maintained until the valproate dose reached 150 mg where the benefits were lost and returned when the dose was again reduced.

Example 2—Treatment of Adult ADHD Sufferers with a Combination of Psychostimulant and Mood Stabiliser: Dexamphetamine and Topiramate In the clinical setting of Example 1, a number of adults with ADHD were successfully treated with a combination therapy of stimulant medication (dexamphetamine) in combination with Topiramate.

Maximum, minimum, average and median dosages used are:

|  | Dexamphetamine | | Topiramate | |
| --- | --- | --- | --- | --- |
|  | mg/d | mg/kg/d | mg/d | mg/kg/d |
| Average | 45.5556 | 0.5283 | 27.7778 | 0.3160 |
| Median | 40.0000 | 0.5155 | 25.0000 | 0.2232 |
| minimum | 30.0000 | 0.3348 | 12.5000 | 0.1389 |
| Maximum | 80.0000 | 0.8889 | 50.0000 | 0.5580 |

Median daily dose of dexamphetamine in this regime is 40 mg/d and Topiramate dose 17 mg/d. Overall doses in this group are in keeping with a relative dosage of 0.56 mg/kg of dexamphetamine and a dose of 0.22 mg/kg of AED (Topiramate).

Clinical example of a 65 year old female with a history of major depression, generalized anxiety disorder and ADHD. Treated for several years on dexamphetamine 30 mg. Ongoing difficulties with interpersonal relationships, disorganization and experienced hyper focusing. Commenced on 25 mg of topiramate. Noted ability to complete tasks, improvement in cognition, able to prioritise and felt as if her memory had been cleared.

Example 3—Treatment of Adult ADHD Sufferers with a Combination of Psychostimulant and Mood Stabiliser: Dexamphetamine and Phenytoin In the clinical setting of Example 1, a number of adults with ADHD were successfully treated with a combination therapy of stimulant medication (dexamphetamine) in combination with Phenytoin.

Maximum, minimum, average and median dosages used are:

|  | Dexamphetamine | | Phenytoin | |
| --- | --- | --- | --- | --- |
|  | mg/d | mg/kg/d | mg/d | mg/kg/d |
| Average | 39.5000 | 0.4998 | 20.94 | 0.28 |
| Median | 35.0000 | 0.4730 | 21.43 | 0.29 |
| minimum | 20.0000 | 0.2410 | 1.00 | 0.001 |
| maximum | 75.0000 | 0.7500 | 75.00 | 1.00 |

Clinical case study of a 60 year old female With a history of major depressive disorder with past hospitalizations and electro convulsive therapy, non verbal learning disorder and ADHD. Diagnosed with ADHD and commenced on dexamphetamine. Despite the stimulant therapy she continued to experience depression, and was a significant suicide risk. Commenced on phenytoin with improvement in ability to read and sustain enjoyable conversation. The dose was initiated at 30 mg and increased to 90 mg. This resulted in a slowing of thoughts and loss of benefit. The phenytoin was reduced to 30 mg with a return of the benefits including improved cognition.

Median daily dose of dexamphetamine in this regime is 35 mg/d and Phenytoin dose of about 20 mg/d. We have noted in many clinical situations that although there was initial benefit on the 50 mg phenytoin dose there was a loss of benefit of the therapy over the proceeding weeks and months. If the medication was then ceased there would be a return of the initial improvement followed by a loss of efficacy over the next week. If the phenytoin was reintroduced at a lower dose the improvement would reoccur and persist usually without further re-titration. Based our clinical experience the preferred stable median dose is between 15 mg and 20 mg of Phenytoin.

Example 4—Treatment of Adult ADHD Sufferers with a Combination of Psychostimulant and Mood Stabilisers: Dexamphetamine and Valproate and Topiramate In the clinical setting of Example 1, a number of adults with ADHD were successfully treated with a combination therapy of stimulant medication (dexamphetamine) in combination with Valproate and Topiramate.

Median daily dose in this regime, a combination of three active agents, is 40 mg/d Dexamphetamine, 120 mg/d Sodium Valproate and 25 mg/d Topiramate.

Clinical case study of a 49 year old man with a history of panic disorder, major depression and ADHD. Initial treatment for panic disorder and further improvement on initiation of dexamphetamine 20 mg a day. Further benefit from addition of sodium valproate, initially increased to 500 mg a day and was successfully reduced to 300 mg and augmented with topiramate 25 mg. Further improvements in interpersonal professional functioning sufficient to return to full-time employment after absence of 3 years.

Example 5—Treatment of Adult ADHD Sufferers with a Combination of Psychostimulant and Mood Stabilisers: Dexamphetamine and Valproate and Phenytoin In the clinical setting of Example 1, a number of adults with ADHD were successfully treated with a combination therapy of stimulant medication (dexamphetamine) in combination with Valproate and Phenytoin.

For the majority in this treatment group, maximum, minimum, average and median dosages used are:

|  | Dexamphetamine | | Valproate | | Phenytoin | |
| --- | --- | --- | --- | --- | --- | --- |
|  | mg/d | mg/kg/d | mg/d | mg/kg/d | mg/d | mg/kg/d |
| Average | 37 | 0.49 | 200 | 2.66 | 27.50 | 0.37 |
| Median | 45 | 0.6 | 200 | 2.67 | 25.00 | 0.33 |
| Minimum | 20 | 0.27 | 100 | 1.33 | 12.5 | 0.17 |
| Maximum | 45 | 0.6 | 400 | 5.33 | 50.00 | 0.67 |

Clinical case example of a male 45 years of age with a history a learning disorder and ADHD. Treated with dexamphetamine therapy to a maximum dose of 25 mg. noted improvements in concentration, still experienced interpersonal difficulties and self organisation remained impaired. Commenced on sodium valproate maximum of 400 mg with good effect. Slowing thoughts and improved both silent and out loud reading. Therapy further augmented and stabilised on phenytoin 20 mg per day with further improvement of the sequencing and organisation of thoughts. Also noted and enhanced motor coordination whilst participating in team sports. Sodium valproate reduced to 160 mg with maintenance of the enhanced benefit.

Clinical case example of a male 23 years of age with a history of ADHD and commenced on dexamphetamine therapy maximum dose 40 mg per day. Continued difficulty with racing thoughts and instability of mood. Sodium valproate commenced with improvement with more organised thoughts stabilised on 100 mg a day. Unable to tolerate higher dose despite motivation, described currently slowing.

Persistent interpersonal deficits and anxiety. Therapy augmented with 12.5 mg phenytoin. Significant improvement in ability to maintain egocentric eye gaze and cognition was able enjoy engage in less effortful social interaction.

Clinical example of a 25-year-old woman with a long history of a major depressive disorder, anorexia nervosa bulimic subtype, ADHD, and borderline personality disorder. Numerous hospitalisations including courses of electroconvulsive therapy and involuntary treatment. She responded to combination of dexamphetamine and sodium valproate 200 mg. but still experienced an ongoing and affective instability in response to unstable interpersonal relationships. With the addition of phenytoin 50 mg later reduced to 25 mg. she described an immediate improvement of stability of affect and clarity of thinking and taking more control over the relationship issues. A significant improvement in egocentric gaze during consultation and improved cognition. It was noted for his initiation of the phenytoin that although dose of 50 mg was therapeutic efficacy was gradually lost remaining at the same dose with increasing side effects particularly cognitive slowing. The phenytoin was ceased and washed out over approximately 7 days. During this time there was initially an improvement in cognitive function followed by a return to pre-medication state. On the reintroduction at a lower dose the initial benefits of the phenytoin returned this time without further loss of efficacy. This clinical observation has been repeated with numerous other individuals with a possible hypothesis developed that there is gradual cerebral accumulation of the antiepileptic or the metabolism of the medication changes with more chronic administration potentially leading to non-linear pharmacokinetics Example 6—Treatment of Adult ADHD Sufferers with a Combination of Psychostimulant and Mood Stabilisers: Methylphenidate and Sodium Valproate In the clinical setting of Example 1, a number of adults with ADHD were successfully treated with a combination therapy of stimulant medication (methylphenidate) in combination with Valproate.

For this treatment group, maximum, minimum, average and median dosages used are:

|  | Methylphenidate | | Valproate | |
| --- | --- | --- | --- | --- |
|  | mg/d | mg/kg/d | mg/d | mg/kg/d |
| Average | 73.3333 | 1.2270 | 100.0000 | 1.7082 |
| Median | 72.5000 | 1.2022 | 100.0000 | 1.4957 |
| minimum | 30.0000 | 0.6383 | 50.0000 | 0.8475 |
| maximum | 125.0000 | 1.6913 | 200.0000 | 3.2258 |

Our data suggests a practical formulation includes a dose of 80 mg of Methylphenidate with a dosage of 100 mg of Sodium Valproate. This formulation is in the expectation of an average subject weight of 75.7 kg. In keeping with previous data the dose range of the Valproate may conveniently be increased to 120 mg.

Clinical case example of a 63 year old male with a history of alcohol dependence, generalized anxiety disorder, PTSD and ADHD. Treated with methylphenidate 55 mg, with improvement in his symptoms of impaired attention and concentration. Continued to experienced difficulty in communication with effortful conversation. Commenced on 100 mg of sodium valproate, with enhanced ability to maintain conversation, improved cognition, improved assertiveness and self organisation.

Example 7—Treatment of Adult ADHD Sufferers with a Combination of Psychostimulant and Mood Stabilisers: Methylphenidate and Topiramate In the clinical setting of Example 1, a number of adults with ADHD were successfully treated with a combination therapy of stimulant medication (methylphenidate) in combination with Topiramate.

For this treatment group, maximum, minimum, average and median dosages used are:

|  | Methylphenidate | | Topiramate | |
| --- | --- | --- | --- | --- |
|  | mg/d | mg/kg/d | mg/d | mg/kg/d |
| Average | 46.6667 | 0.8448 | 24.8333 | 0.4265 |
| Median | 45.0000 | 0.8511 | 25.0000 | 0.4808 |
| Minimum | 40.0000 | 0.7051 | 12.0000 | 0.2553 |
| maximum | 55.0000 | 0.9783 | 37.5000 | 0.5435 |

Clinical case study of female 20 yrs with a history of anorexia nervosa, borderline personality disorder, major depression and ADHD. Initial response to methylphenidate remained inconsistent, unstable, disorganized with frequent relapses of her eating disorder and major depression. Commenced on the oros extended release methylphenidate and augmented with 25 mg of topiramate resulting in improved organisation, cognition, enhanced interpersonal functioning, and ability to sustain egocentric eye gaze.

Example 8—Treatment of Adult ADHD Sufferers with a Combination of Psychostimulant and Mood Stabilisers: Methylphenidate and Phenytoin In the clinical setting of Example 1, a number of adults with ADHD were successfully treated with a combination therapy of stimulant medication (methylphenidate) in combination with Phenytoin.

For this treatment group, maximum, minimum, average and median dosages used are:

|  | Methylphenidate | | Phenytoin | |
| --- | --- | --- | --- | --- |
|  | mg/d | mg/kg/d | mg/d | mg/kg/d |
| Average | 60.0000 | 0.6530 | 31.2500 | 0.3476 |
| Median | 60.0000 | 0.7854 | 25.0000 | 0.3457 |
| minimum | 15.0000 | 0.1515 | 25.0000 | 0.2525 |
| maximum | 105.0000 | 0.8898 | 50.0000 | 0.4464 |

From our clinical experience a practical formulation may include a dose of 60 mg/d of Methylphenidate with a dosage of about 20 mg/d of Phenytoin. This formulation is in the expectation of an average subject weight of 75.7 kg.

Clinical case study of a 21 year old male 120 kg. Patient has a history of ADHD, school and interpersonal difficulties. Diagnosed with ADHD in childhood inconsistent stimulant therapy during adolescence non-compliance between 18 and 20 years of age. Recommenced methylphenidate 120 mg per day. Remain disorganized and inconsistent with taking medication, resultant ongoing interpersonal difficulties. Commenced 50 mg phenytoin noted improved cognition with increased confidence in interpersonal relationships, greater awareness of appropriate boundaries and behaviour. More able to organise and not forget to take his medication.

Example 9—Treatment of Adult ADHD Sufferers with a Combination of Psychostimulant and Two Mood Stabilisers: Methylphenidate, Valproate and Phenytoin In the clinical setting of Example 1, a number of adults with ADHD were successfully treated with a combination therapy of stimulant medication (methylphenidate) in combination with Phenytoin and Valproate. For this treatment group, convenient effective daily dosages are Methylphenidate 40 mg/d, Valproate 100 mg/d, and Phenytoin 50 mg/d. As suggested, the doses may be adjusted such that an optimal dose within the objectives of therapy are achieved, including, say, a daily dose of 80 mg/d of Methylphenidate.

Clinical case study of adult female with a history of ADHD depression, anorexia nervosa bulimic subtype, borderline personality disorder. Several serious suicide attempts, multiple self harm episodes and a prolonged admission to hospital. Commenced on methylphenidate with reasonable improvement. She was still unable to control her thoughts; verbal communication remained impaired with difficulty articulating ideas. Improvement on commencement of sodium valproate maximum dose of 150 mg. Later augmented with phenytoin 50 mg and the dose of sodium valproate reduced to 100 mg Pervasive and robust psychosocial improvement, Reading and egocentric gaze improved. Improvement in cognition with no further episodes of self harm. She now has control of eating disorder with weight stability.

Example 10—Treatment of Adult ADHD Sufferers with a Combination of Psychostimulant and Two Mood Stabilisers: Dexamphetamine and Sodium Valproate and Oxycarbamazepine 50-year-old man with a history of ADHD is commenced on dexamphetamine 40 mg daily and sodium to operate 400 mg daily. This was augmented with the addition of 37.5 mg of oxycarbamazepine with significant improvement in his cognitive functioning improved again on dose increased to 75 mg. Switch to the older medication of carbamazepine because of cost though found to be less effective and now recommenced low-dose oxycarbamazepine.

Example 11—Enhanced Treatment of Dysthymia

Dysthymia is a mood disorder that falls along the depression spectrum. It is considered a chronic and long-lasting form, but with less severity and intensity than a major depression. Dysthymia tends to be more constant, lasting for longer periods. In both conditions, a person can have a low or irritable mood, lack of interest in things most people find enjoyable, and a loss of energy. Appetite and weight can increase or decrease. Individuals may sleep too much or have trouble sleeping. They may have difficulty concentrating, being indecisive and pessimistic, with a poor self-image. Individuals with dysthymia have a greater-than-average chance of developing a full-blown episode of major depression.

This disorder is sometimes called "double depression" because the intense episode exists with the usual feelings of low mood. Dysthymia can begin in childhood and as a result individuals with dysthymia tend to believe that depression is a part of their character. Individuals may not even think to talk about the depression with doctors, family members or friends. Dysthymia, like major depression, tends to run in families and is two to three times more common in women than men.

The inventor has noted in the clinical setting that individuals suffering with symptoms consistent with a diagnosis of dysthymia, experience a significant abatement from their negative and sometimes intrusive thought patterns on commencement of a low dose anti-epileptic drug. The inventor has also noted in the clinic that the beneficial effects that are noted on commencement of this combination can be further enhanced synergistically, by the use of a psycho-stimulant. These individuals may or may not meet the full criteria for a DSM IV diagnosis consistent with ADHD. However, the inventor has found that individuals with a subthreshold diagnosis of ADHD can benefit from the use of low dose psycho-stimulants with the low dose anti-epileptic drug.

A number of individuals with symptoms of dysthymia report that the depression has been present since adolescence, and finally present in the clinic, after an acute major depressive episode. They are able to achieve a partial resolution from the symptoms of depression with appropriate pharmacological and psychological treatment. Unfortunately, their negative thought patterns are more persistent and can be misinterpreted as a failure to adequately respond to antidepressant therapy. In actuality these symptoms predate the acute episode, and it is not surprising therefore that they don't abate following treatment. The inventor has noted that the addition of a low dose anti-epileptic drug results in an effortless control of these negative thoughts and an improvement in social cognition. These subsequent outcomes lead to an improvement in general interpersonal functioning, which in itself contributes to psychosocial stability. From clinical observations these changes appear robust and long-lasting. There does not appear to be a development of treatment resistance to the low dose anti-epileptic drug. On the contrary it appears that the improvements observed act in synergy with each other, leading to continued and sustained improvement.

The treatment of the underlying dysthymia also improves both during and between acute depressive episodes with the low doses anti-epileptic drug. It is postulated that similar benefits may also occur in the treatment of an individual with a diagnosis of a major depressive episode who experiences concomitant deficits in the area of social cognition, eye-gaze, negative and intrusive cognitions and other conditions secondary to ocular motor dysfunction.

Clinical case study of a 66 year old male. History of school difficulties, Dysthmia, alcohol abuse major depressive disorder, PTSD and ADHD. Describes low-grade depression since early childhood. Accumulated additional diagnoses and experienced long term interpersonal difficulties. Several long term psychiatric admissions. Acute episodes of depression, partially treated without complete remission. Diagnosed with ADHD and treated for three years with moderate improvement. Commenced sodium valproate 100 mg a day noted that he could read without distraction. Comfortable with his own thoughts which he had never been previously able to tolerate. Also found himself enjoying conversation, which he had never noted before.

Example 12—Treatment of Developmental Dyspraxia

Developmental dyspraxia is a heterogeneous range of developmental disorders affecting the initiation, organisation and performance of action. It entails the partial loss of the ability to coordinate and perform certain purposeful movements and gestures in the absence of motor or sensory impairments. The concept of developmental dyspraxia has existed for more than a century, but differing interpretations of the terminology remains. Developmental dyspraxia is a life-long condition that is more common in males than in females; the exact proportion of people with the disorder is unknown since the disorder is difficult to detect. Current estimates range from 5%-20% with at least 2% being affected severely. Developmental dyspraxia has been described as the 'difficulty of getting our bodies to do what we want when we want them to do it', and is considered to be significant when it interferes with the normal range of activities expected for a child of their age. It is not due to a general medical condition, but it may be due to immature neuronal development.

It is described as having two main elements:
1 Ideational dyspraxia—Difficulty with the ideation and planning of a sequence of coordinated movements.
2 Ideo-Motor dyspraxia—Difficulty with executing a plan, even when known.

Dyspraxia is often associated with problems of perception, language, thought and cognition. Developmental verbal dyspraxia is an example of ideational dyspraxia, which causes linguistic or phonological impairment. Key features include: difficulties controlling the speech organs, and making speech sounds; difficulties sequencing the sounds and slow language development. Developmental co-ordination disorder is representative of difficulties with fine motor co-ordination which lead to problems with handwriting. These difficulties can be attributed to either ideational or ideo-motor difficulties. Problems associated with this area may include: delays in learning basic movement patterns, slow writing speed and incorrect pencil grip, which often results in pain and fatigue in the hand during writing activities. Whole body dyspraxia features difficulties of gross motor coordination impacting on developmental targets such as walking, running, climbing and jumping. Problems associated with this area may include: poor timing and balance; difficulty combining movements into a controlled sequence and remembering the next move in a sequence; problems with spatial awareness, lower muscle tone and general clumsiness.

Assessments for dyspraxia typically require a developmental history, detailing ages at which significant developmental milestones, such as crawling and walking occurred. Screening for motor skills includes activities designed to indicate dyspraxia including balance, physical sequencing, touch sensitivity, and variations of walking activities. A baseline motor assessment establishes the starting point for developmental intervention programs.

Individuals with dyspraxia sometimes have difficulty moderating the amount of sensory information their body is constantly sending them, and as a result individuals are prone to sensory-induced panic attacks. Many physical tasks may cause frustration and isolation, due to the fact that these tasks can be quite challenging for the individual with dyspraxia. Fatigue is common because so much extra energy is expended while trying to execute a sequence of physical movements correctly. Some individuals suffer from hypotonia, as reflected in their low muscle strength and endurance and subsequently even the simplest physical activities may quickly cause soreness and fatigue, depending on the severity of the hypotonia. Hypotonia may also exacerbate an individual's already compromised balance system to the point where it is necessary for them to lean on sturdy objects for support.

Many of the individuals treated at this clinic, with a diagnosis of ADHD and/or pervasive development disorder such Asperger's Syndrome or autism also present with symptoms consistent with a diagnosis of a developmental coordination disorder. They are often described as 'unco' (unco-ordinated) by their peers and experience victimization, poor self-esteem and frustration as a consequence of their poor coordination. The inventor has noted a significant improvement in physical coordination in these individuals when treated with a low dose anti-epileptic drug, with or without psycho-stimulants. Individuals have described a sense of having more time to coordinate movements and to understand and integrate their own activity appropriately within a team sport such as soccer, which has previously eluded them. Individuals have felt frustration at being able to practise repeatedly an activity or skill only to be unable to put it into practice when required, within the play of a match. It is proposed that individuals were previously unable to process and plan their own coordination but remain aware of the general activity in which they were participating. The enhanced ability has resulted in improved confidence and self-awareness.

Individuals have noted general physical improvements and confidence in diverse activities from being able to walk without awkwardness, to being able to undertake complex coordinated activities such as kicking a moving ball and remaining aware of balance and intended outcome of their movements.

It is postulated that these individuals have been able to automatise sufficiently the many components of a range of movements, enabling the focus of their attention to fix on the most complex aspect of the movement, with the confidence that the more simple movements would occur with some degree of reliability.

16 year old male. History of autism with a associated motor and verbal tics, developmental dyspraxia, school refusal and ADHD. Titrated to a maximum of methylphenidate 95 mg daily. Limited improvement with poor compliance. Initialised on a Sodium valproate dose of 50 mg, in combination with stimulant. Needed to increase dose up to 100 mg. Patient experienced improved coordination, improved school attendance, improved cognition and report grades and a significant benefit for coordination. He is now able to enjoy team sports, and is now able to coordinate his actions during a game. He describes that whilst playing football the experience of having more time on the ball whereas previously he always felt rushed when kicking the ball. He is now able to take his time and anticipate the outcome of his shot. He has also been able to appreciate the participation of other players in the team, resulting in better integration. His level hyper-focus has also reduced whereas previously he noted that he could demonstrate good ball skills when practicing alone. When faced with a team situation he was overwhelmed unable to both focus on the other players and on his skills. This led to him becoming clumsy and awkward in his basic skills leading to frustration and a perception that he could not contribute to the team despite his ability to perform well in practice.

44-year-old male diagnosis of ADHD, commenced on dexamphetamine dose of 25 mg daily this was augmented with atomexetine 60 mg and sodium valproate 150 mg. Significant improvement in psychosocial functioning and maintained on this therapy for two years prior to the addition of phenytoin 25 mg. This resulted in an improvement in coordination most notable when playing ball sports. He had always been aware of his poor coordination especially evident in team sports. Improved on commencement of the phenytoin. This medication was ceased and recommenced on a number of occasions in an attempt to try and identify whether this was the cause of the improvement. There was a close temporal relationship between the benefits and the medication. These improvements have continued and been further enhanced over 12 months.

Example 13—Treatment of Eating Disorders

Eating disorders (such as Anorexia Nervosa and Bulimia Nervosa) are conditions associated with high morbidity and, in the case of Anorexia Nervosa, a significant mortality rate. Contemporary research to date, which describes the treatment of eating disorders, uses years to relapse and partial remission as the key measurable outcome. It is likely that eating disorders are heterogeneous in their origin and despite the interest in both clinical and research areas, the treatment is often complex and at times frustrating for both the clinician and individual.

Isolated case studies of individuals with an eating disorder and a co-morbid diagnosis of Attention Deficit Hyperactivity Disorder (ADHD) have been identified. Double-blind studies using methylphenidate have shown a suppression of bulimic symptoms, although it was thought that these effects were only short-lived. While these studies may reflect random chance events, they may in fact represent a previously unrecognised association between eating disorders and ADHD. This has been demonstrated in studies that report the successful treatment of ADHD with psycho-stimulants, with a simultaneous and significant improvement in the symptoms of an individual's co-existing eating disorder.

Studies have suggested that females with a diagnosis of ADHD are more likely to present with cognitive impairments, anxiety disorders, depression and low self esteem than their male counterparts, but are less likely to show severe behavioural disturbances and conduct disorder. Females also often display a greater prevalence of co-morbid internalising and learning problems. Disorganisation is one of the more predominant symptoms experienced by females with ADHD and while some women appear to be highly organised, obsessional and spending hours over-organising, in actuality they fear the negative ramifications of failing to organise efficiently. It is proposed that this manifest behaviour is a reaction or adaptation to the internal sense of chaos often felt by women with ADHD.

The need for a sense of control and mastery, which is often deficient in ADHD, is also seen in individuals with eating disorders. Individuals with Anorexia Nervosa experience an overwhelming sense of ineffectiveness and the ritualistic control of food and weight can be viewed as a substitute for a sense of purpose and accomplishment.

It has been clinically noted that the onset of eating disorders frequently coincides at the time of many physical, psychological and academic adaptations and challenges, generally occurring during the early high school years (12-15 yrs). This time of transition is more difficult if the individual experiences impairment in higher executive functioning and cognitive deficits consistent with a diagnosis of ADHD particularly of the inattentive subtype or a sub threshold disorder. These individuals often have impairments in the area of social cognition and are noted to have difficulties sustaining egocentric gaze during verbal communication. These individuals are typically female and are more likely to be missed than the hyperactive or combined subtype of ADHD, which is usually diagnosed at an earlier age. This cluster of presenting difficulties may also make them eligible for a diagnosis of ASD or symptoms consistent with sub threshold diagnosis of ASD but impairment in social communication. Teachers often describe these children as less disruptive in the classroom, but they often have higher degrees of social impairment, unhappiness, and social anxiety or depression than the combined subtype of ADHD.

The inventor has treated more than 20 patients who have been diagnosed according to DSM IV of the dual conditions of an eating disorder and ADHD. It is postulated that not only is this dual presentation common, but with appropriate treatment of the dual diagnosis there can be a significant improvement in the overall prognosis compared with the usual course of the eating disorder. The combination of using a psycho-stimulant with a low dose anti-epileptic and mood stabilizer (anti-epileptic drugs) has demonstrated significant improvements in being able to maintain egocentric gaze and social cognition. There can also be a concomitant reduction of both the pervasive loss of self-effectiveness and the long-term emotional disconnection, which are closely associated with eating disorders. In some clinical cases there has been further enhancement of the therapeutic effects of the low dose mood stabilizers, when two or more are combined at low dose levels.

The inventor has clinically noted that individuals with complex co-morbidities, a long history of impairment, with multiple acute episodes of severe illness, gain further benefit in treatment by a combination low dose therapy of anti-epileptic drugs. These individuals often describe an unremitting and disruptive thought pattern that is characterised by the absence of any pervasive mood disturbance. The intrusive and usually repetitive thoughts are almost always difficult to control and require significant, effortful concentration to suppress. All aspects of functioning are disrupted by these intrusive thoughts, the content of which can be directly related to the eating disorder and self-deprecating themes. Further, even when these negative cognitions are controlled they can be replaced by less negative, but equally distracting thoughts. As a result, the effort involved in simple tasks such as social interaction is greater than normal, as the whole interaction is compromised by the individual's attempts to suppress the intrusive thoughts. The individual is faced with the difficult task of attempting to communicate in the face of multiple and unremitting cognitive disruptions. Of particular note in the understanding of the social cognitive deficits associated with eating disorders who are unable to connect during normal social interaction and establish the normal egocentric eye gaze. They by necessity focus on other visual aspects of the interaction, frequently the others physical form as well as their own. This further reinforces the physical aspects of the abnormal eating disorders cognitive processes.

It is postulated that the focus during social conversation becomes centered on the communicative process rather than the content, which limits the individual's comprehension and ultimately any potential positive social outcomes. the clinical approach has been to control the pace and intrusiveness of these thoughts. The combination of a psycho-stimulant and a low dose anti-epileptic drug often results in a significant abatement of these symptoms. In a number of severely affected individuals where the control over intrusive thoughts does not occur with this combination, the approach can be adapted using further augmentation.

The use of sodium valproate at low dose levels can then be titrated to a level that does effectively control these thoughts. This may or may not be at the therapeutic dose used in the treatment of bipolar disorder. The inventor has observed in these complex and severe clinical cases that there still remains a significant social deficit which is not improved by further escalation of the sodium valproate. A more successful approach has been to use a low dose of a second mood stabiliser. Following this strategy there is frequently a robust enhancement of the cognitive processing, egocentric eye gaze and overall psycho-social functioning. It was notable that in many cases the improvement occurred despite the presence of several factors normally associated with predictors of poor prognosis, including concomitant affective disorders, personality and substance disorders, a greater than 35% weight loss, suicidal behaviour and significant family conflict. Despite the presence of poor prognostic indicators, the cognitive improvements occurred concurrently with a reduction in the dysfunctional, typical eating disorder thought patterns and often an improvement or cessation of bulimic/anorexic behaviour. Further, in individuals with a sub-threshold ADHD presentation, the addition of a low dose anti-epileptic drug (less than 0.1-0.2 mg/kg) in combination with low dose psycho-stimulant such as dexamphetamine has also been found to be very effective.

Clinical example of a female 20 yrs old with a history of anorexia nervosa, borderline personality disorder, major depression and ADHD. Initial response to methylphenidate remained inconsistent, and continued to present as unstable, disorganized with frequent relapses of her eating disorder and major depression despite the use of the 45 mg of extended release methylphenidate. Later augmentation with 25 mg of topiramate resulted in improved organisation, enhanced interpersonal functioning, improved cognition and able to sustain egocentric eye gaze.

Example 14—Enhanced Compliance with Medication

Adherence with pharmacotherapy is a long-standing and difficult problem for many individuals with a range of clinical disorders. In clinical populations such as individuals diagnosed with a psychiatric disorder the challenge of remembering to take accurately timed and appropriate dosages of medication is often a limiting factor in their general treatment, which reduces the benefit of pharmacotherapy. It has been estimated that in the treatment of complex medical conditions compliance rates of just over 30% are not uncommon. (Blonde 2000) This situation is often further complicated by the need to take complex pharmaceutical regimes, including at times medications that have negative side-effects for attention and concentration, which may further impair the ability to adhere to treatment regimes. These compliance issues are experienced in all areas of medicine. The benefits of remembering to take medication at appropriate times and in appropriate doses would have an enormous impact in the cost effectiveness of pharmacotherapy and the ability to improve clinical outcomes so much so that medication non compliance has been called "America's other drug problem" (Stephenson 1999).

Medication compliance is the single factor that is often the most restrictive factor in providing a desired therapeutic outcome. We suggest a combination of a low dose AED with other pharmaceutics could enhance adherence to medication by improving the ability to effortlessly attend and focus to the requirement to take the medication. Ideally this will be in the form of a single composition including the low dose AED or two low dose AED's and the other pharmaceutical agent An example from the clinical population has been with individuals diagnosed with ADHD. The continuation rate of stimulant therapy beyond 12 months, as assessed by script analysis, is frequently reported in naturalistic settings as less than 33%. The inventor has noted similar findings in clinical populations of individuals referred for assessment of adult ADHD and treated with psycho-stimulants alone. These medications are prescribed because of their known action to effectively enhance attention, leading to increased hyper focusing on tasks of interest and tasks at hand. This often results in not attending to other less interesting areas of activity or disregarding tasks that are not actually present. As a result, remembering to consistently take medication is not given a priority over the current and attention engaging task.

The inventor has noted that in treating individuals (with and without ADHD) with a low dose anti-epileptic drug, with or without psycho-stimulants, there has been improvement in the ability to manage the organisation and planning required to consistently take medication. This relatively simple and profound improvement in self-organization, has consistently led to subsequent improvement in psycho-social functioning. Clinical observations suggest that the core area of improvement with low dose anti-epileptic drugs appears to be in the effortless ability to sequence and organize thoughts. As a result, taking medication becomes an automatic activity which doesn't require a high level of attention and motivation.

It is proposed that improvement in effortless attention enhances the cognitive skills required to automatically and effectively organize complex tasks, such as taking medication. The individual experiences an improvement in the ability to efficiently and effectively attend to a task in hand, without also needing to expend extra cognitive effort to remember which medication to take and at what times. The improvements noted in the clinical populations, which include adults treated for ADHD, are particularly relevant. Many individuals are on a treatment regime that does not involve long acting medication, and hence the task of remembering to take the stimulants up to six and seven times a day, is often too demanding to maintain. However, in the clinical setting, and despite potentially confounding variables, a twelve-month compliance rate was achieved with a combination of a psycho-stimulant and a low dose anti-epileptic drug, in excess of 80%. This dramatic improvement has been noted in a relatively large sample of individuals in clinic.

Clinical example of a 41 year old female with a history of marijuana dependence, alcohol abuse, borderline personality traits and ADHD. Commenced on dexamphetamine 40 mg daily with a short term improvement in concentration but experienced ongoing difficulty with distraction and disorganisation. Augmentation with sodium valproate was initiated at a dose of 400 mg daily. This was too sedating and the dose was subsequently reduced to 100 mg with the patient experiencing improved efficacy, cognition, organisation and compliance with medication. The latter resulted in a significant overall improvement from reliable adherence to all prescribed medication.

Further clinical example of an 82 yr old man with a complex pharmaceutical regime for the treatment of both psychological and physical conditions without a comorbid diagnosis of ADHD, ASD or dementia. Sodium valproate at dose of 100 mg was added. This resulted in an enhanced ability to track his thoughts with less effort, becoming more organised in all aspects of his life including his ability to consistently adhere to his treatment regime.

62-year-old woman with a history of anxiety and depression. No evidence cognitive impairment or ADHD. Described having increasing difficulty in self organisation including adherence to medication. Commenced on 25 mg of phenytoin, noted improved self organisation and ability to plan ahead without effort. This medication was ceased and recommenced, the functional changes coincided the alterations therapy.

Example 15—Treatment of Addictions

In the inventor's clinical experience, combinations of the invention have been found to reduce the cravings and consumption of alcohol. It is hypothesized that this combination has reduced the underlying desire and need for the alcohol. This is in keeping with the knowledge that the effect of the alcohol is in part mediated through impaired cerebellar function.

Addiction to amphetamines poses a number of unique challenges. Use of psychostimulants alone (such as dexamphetamine) has been unhelpful in the treatment of amphetamine and cocaine addiction. The inventor's clinical experience indicates that treatment with combinations of the invention reduces the desire and associated dependence on these substances.

In a clinical example, a 45 year old man with a history of methamphetamine use was treated with 50 mg/d of dexamphetamine and 100 mg/d Valproate. The patient subsequently described a robust improvement in attention and concentration abilities. He subjectively described the stability and functional benefit similar to that he had only experienced during his Methamphetamine misuse. This stability was not noted when he was taking dexamphetamine alone over 6 months.

Two additional patients have presented with co-morbid diagnoses of ADHD and methamphetamine addiction. Both have responded well to 50 mg/d dexamphetamine in combination with Valproate at 50 to 100 mg/d.

Clinical example of a female 45 yrs with a history of substance dependence in late teens and early 20s. Increasing drug misuse in last five years with alcohol and marijuana dependence. Diagnosed with ADHD and commenced on dexamphetamine max dose 45 mg a day, with reduction of ADHD symptoms. With continued drug misuse she was commenced on sodium valproate with an initial dose of 50 mg that was increased to 200 mg. Patient experience a reduced dependence on marijuana and ceased alcohol consumption. Described improvement in ability to control thoughts which reduced the need to self-medicate.

Example 16—Eye Gaze

Most individuals automatically sustain eye gaze during social interactions, both when taking the speaker and listener roles. Individuals in their first social connection briefly make direct eye contact (which is referred to as the initial eye gaze reflex) and then continue to maintain eye gaze throughout the social interaction. Individuals find a balance between fixed gaze and averted, as either may send an inappropriate social message—fixed gaze communicates aggression and dominance, and may even be considered threatening, while averted gaze can communicate boredom, lack of interest and disengagement. The initial eye gaze reflex appears to be an evolutionary process common to humans and other mammals. The importance of being able to connect with others and determine either security or potential danger can be readily understood. It seems that in this moment the priority is to make a rapid visual assessment. After this initial contact response a well-developed and sophisticated social interaction can follow. It is proposed that eye contact and egocentric gaze hold precedence over other aspects of communication in impaired psychological functioning, thereby inhibiting more mature or sophisticated patterns of social interaction. Consequently, the individual develops an adaptive response to a dysfunctional situation.

After the initial eye gaze reflex between communicative partners, there is a rapid habituation of the reflexive response, where the visual importance is downgraded to enable sufficient cognitive attention to allow ongoing verbal communication and social interaction. Mental energy is diverted to cognitive processes such as sequencing, integration, filtering, organizing thoughts and prioritizing, and the language demands of social discourse such as articulation, word finding, sentence construction, grammar, cohesion and narrative skills. During any social interaction there is reciprocity of eye gaze between the communicative partners that sustains the social connection and works towards building and enhancing the social relationship.

It is postulated that individuals who fail to habituate this initial eye contact reflex may become overloaded by the demands of information and sensory processing required through sustained eye contact. Individuals who experience difficulties in eye gaze are open to two adverse outcomes. If individuals feel unable to break the eye contact, their focus and attention is distracted, gazing intently and often fixedly at the other person. Alternatively, individuals may forcibly break eye contact, averting their gaze in order to initiate verbal conversation. They continue through the social interaction, failing to maintain a social connection with the other person through any casual eye contact. Individuals who have experienced these responses describe an inability to find the desired words, dysfluency, rambling and poorly organized sentences and ideas, or that their 'mind goes blank'. They may also have the experience of a secondary internal dialogue. This is as if they are answering, participating and commenting on the conversation in their head. This should not be considered as language as it often is if not impossible to articulate verbally in real time the content in real time. As the ideas and responses can often be multiple requiring considerable effort to select the most valid or appropriate response. Unfortunately despite these thoughts and responses being selected almost spontaneously in the conversation, by the time they are converted into language the response is no longer in real time, resulting in frustration and a degree of disconnection from the other.

Social interaction and social discourse requires an effortless and almost unconscious ability to maintain a socially acceptable level of eye contact (socially acceptable levels vary amongst different cultures). Competent communicators are able to gauge the emotional responses or levels of comprehension of the other person by effortlessly monitoring eye gaze. Signals of boredom, animosity, and lack of understanding for example, are all generally reflected in the eyes and subtle facial gestures, which are being constantly monitored unconsciously and automatically. A person's conversation can be modulated then in accordance with these non-verbal signals. If eye contact is too distracting and places too great a load on a person's social cognition, it becomes an effortful task to over-ride and conversation quickly breaks down.

If the individual attempts to maintain the eye contact in such situations, the resultant conversation and social interaction appear to take on certain characteristics. We have consistently observed the following set of features in this type of speaker style:
1. Loss of mental flexibility
2. Reduced prosody
3. Dysfluency with hesitations and stuttering
4. Inability to find the desired words
5. An experience of the mind 'going blank'—a sudden loss of ideas
6. Use of excessive facial gesturing, compensatory for lack of verbal content
7. Rapid onset of mental fatigue and difficulty sustaining attention.

We have also observed individuals who attempt the second strategy of averting their gaze during conversation. The lack of egocentric gaze during a conversation can result in the speaker not noticing cues such as nodding or facial signs of confusion. Features of such speakers include:
1. Rambling and poorly organized sentences and ideas
2. An increase in the effort of speaking
3. Frequent repetition of ideas, words or sentences
4. The development or worsening of verbal or motor tics, in particularly anxiety provoking situations
5. Rapid onset of mental fatigue and difficulty sustaining attention.

In more severe forms of impairment the maintenance of eye contact during the listening turn can present different characteristic signs when it becomes effortful, particularly if the listener is trying to appear receptive. The natural reciprocity and flow of conversation is lost. Effortful listening can show signs of:
1. Excessive and inappropriate nodding, often too early
2. Completion of the speaker's sentences
3. Excessive facial gestures
4. Rapid onset of mental fatigue and difficulty sustaining attention.

Successful social interaction demands the ability to ignore or filter out various potentially distracting sensory stimuli—such as an annoying mechanical sound, a background conversation, an uncomfortable tactile sensation from clothing or an uncomfortable chair, a bright or flashing light, just to name a few common sensory distracters.

The suppression or habituation of initial eye gaze reflex is important, and where it doesn't occur, an individual can be handicapped in many aspects of life. This difficulty can be observed to severe levels in the Autistic Spectrum Disorders, However, even what might be considered mild to moderate difficulties in eye gaze, can be sufficiently disabling to reduce the adequacy of social interaction. This in turn, together with any associated co-morbidities, leads to the significant vulnerability that occurs in individuals with complex and disabling psychiatric illness. Difficult and effortful social interactions, lead to increasing social isolation through avoidance of social situations, which in turn leads to poor peer relations, lack of social resources and networks, and a potentially overwhelming sense of loss of connectedness with others.

Initial eye gaze in any contact between people is consistently towards the eyes. The intensity and persistence of the sensory stimulus is suppressed to enable non-effortful attention to and processing of other more relevant information. If suppression or habituation does not occur, the system becomes overloaded and socially acceptable levels of eye contact are not maintained. The ability to effectively manage the sensory information from eye gaze may be the underlying core deficit in disorders that present symptoms of social dysfunction.

There is a definite potential through the proposed treatment to reverse this decline and social isolation due to gaze impairment and eye movement dysfunction. Importantly from our early data we are predicting that treating this condition as soon as it can be identified (e.g. through a simple task such as rapid automatic naming) may prevent the accumulation of negative life events, which is often sadly associated with this dysfunction, and hence exacerbating the generally negative outcomes associated with the original diagnosis.

Diagnoses that are implicated by this hypothesis include, but are not exclusive to: affective disorders (such as Bipolar Disorder, Recurrent Major Depression); Schizophrenia; eating disorders (such as Anorexia Nervosa and Bulimia Nervosa); cognitive disorders (such as Mild Cognitive Impairment); developmental disorders (such as developmental dyspraxia and Tourette Syndrome); and personality disorders.

Eye gaze has been reported in a great variety of fields of study, from exploring the eye gaze patterns of individuals with autism, to trying to delineate how eye gaze is related to how individuals think. Much of the research is laboratory based possibly to limit the action of other variables. When therapists (psychologists, psychiatrists, speech pathologists) have attempted to train appropriate and socially acceptable eye gaze they are constantly challenged by the number and variety of subtle variables that make eye gaze so much more complex than it appears. As competent communicators, eye gaze comes automatically and relatively easily. It is only when we meet someone who has an abnormal eye gaze that we appreciate the complexities. As competent communicators we may not even register what it is about someone else that makes it so difficult to sustain a conversation with that person.

Eye gaze is very much a reciprocal process. Both communicative partners signal engagement in the social interaction principally through eye gaze. However, other non-verbal cues support the quality of the eye gaze. Non-verbals such as facial expressions, body posture, head posture, hand movements and body proxemics all act together with eye gaze to show our engagement in social interactions. The subtleties of each facet, in addition to the complexity of the whole, make it an intriguing field of study, but equally very challenging and often quite subjective.

We have found through clinical experiences that the impact of low dose anti-epileptic agents on eye gaze is dramatic and plays a central part in the general hypothesis underlying our work. Through a number of empirical tests such as using facial tracking technology, direct and indirect eye movement assessment tools, we have been able to quantify the changes pre- and post-pharmaco-therapeutic intervention. Without the benefit of the therapeutic effect as outlined in this invention, it is otherwise difficult to maintain objectivity, in describing and defining the processes behind eye gaze.

We have also been able through to use of infrared eye movement recording devices identify variations in saccadic eye movements during social interaction social interaction and other experimental situations. This has enabled us to objectivity record the various eye movement patterns in individuals who can maintain egocentric eye gaze during conversation and those who cannot. The cause of these deficits can either be developmental or degenerative. We have further able following treatment with low dose AED's with and without psycho stimulants to demonstrate improvement of these patterns of eye movements. There is also a relationship between the ability to speak and be egocentric eye gaze in this experimental situation. We have further noted alterations in the prosody of the patient in that dialogue this also appears to have some relationship with the ability to maintain egocentric eye gaze during this experimental situation.

Example 17—Sleep Disorders

Sleep disorder (somnipathy) is a medical disorder of the sleep patterns of an individual. Some sleep disorders are serious enough to interfere with normal physical, mental and emotional functioning. Dysomnia is a broad category of sleep disorders characterised by either hyper-somnolence or insomnia. The three major subcategories include intrinsic (i.e., arising from within the body), extrinsic (secondary to environmental conditions or various pathologic conditions), and disturbances of circadian rhythm. It is often found that individuals who fall into the first category often have difficulty in the initiation of sleep due to difficulties in controlling and suppressing intrusive thoughts. This may or may not occur in individuals with a diagnosis of ADHD, Generalised Anxiety Disorder or some other psychiatric condition. It can also occur in individuals who would not meet the criteria for a psychiatric condition apart from experiencing a sleep disorder. These individuals are often characterised by symptoms of initial insomnia. They are unable to switch off their minds in order to fall asleep.

Many individuals who suffer from sleep disorders and/or other disorders have had difficulty sleeping since childhood. They are often physically and mentally exhausted, and on waking overnight, they have difficulty returning to sleep because of ongoing, intrusive thoughts. Individuals may or may not report these thoughts to be racing or intrusive during the day. During the night-time however they have difficulty controlling and dismissing them. The combination of a low dose anti-epileptic drug has been effective in assisting the initiation of sleep and the resumption of sleep after waking during the night. This intervention has the added benefit of acting as a cerebral enhancer and not as a depressant, which is the action of the sedative hypnotics, usually used in the treatment of sleep disorders.

In this context, restless legs syndrome can be placed in the same category as other sleep disorders. In ability to suppress effortlessly these sensations of movements from limbs can be seen as a similar receptive experience as the inability to suppress intrusive thoughts. Without the ability to effortlessly prioritise and then downgrade appropriately such sensations as might emanate in the restless legs syndrome, they become and intrusive experience and thus prevent the initiation of sleep. The combination of a low dose AED with a psychostimulant can have a significant and beneficial therapeutic effect.

The 45-year-old male history of ADHD. Improvement on commencing dexamphetamine 25 mg daily. Chronic sleep difficulties with initial insomnia and frequent middle insomnia after waking. Noted on commencement of the sodium valproate that less effort was required to initiate sleep, he was able without effort and therefore without conscious awareness to control his thoughts and not attend to the sensations of restless in his legs. Also noted that for the first time was able to have relax and rest during the day it was not having to expend considerable effort staying awake when less interested or stimulated during the day time. It was described as the ability to control when and where you wished to initiate sleep. Previously he had to physically and mentally exhausted himself prior to resting and conversely during the day after adequate sleep would feel tired and exhausted.

Example 18—Movement Disorders: Parkinson's Disease

Parkinson's disease is a degenerative disorder of the central nervous system that often impairs the sufferer's motor skills, speech and cognition, as well as other functions. It is both chronic and progressive. Parkinson's disease belongs to a group of conditions called movement disorders and is characterised by muscle rigidity, tremor, a slowing of physical movement and, in extreme cases, a loss of physical movement. Secondary symptoms may include high level cognitive dysfunction and subtle language problems. Typical non-motor symptoms include; Executive dysfunction, characterized by difficulties in: differential allocation of attention, impulse control, set shifting, prioritizing, evaluating the salience of ambient data, interpreting social cues, and subjective time awareness. This complex is present to some degree in most Parkinson's patients; it may progress to: dementia: a later development in approximately 20-40% of all patients, typically starting with slowing of thought and progressing to difficulties with abstract thought, memory, and behavioral regulation. Hallucinations, delusions and paranoia may develop. Short term memory loss; procedural memory is more impaired than declarative memory. Prompting elicits improved recall. Non-motor causes of speech/language disturbance in both expressive and receptive language: these include decreased verbal fluency and cognitive disturbance especially related to comprehension of emotional content of speech and of facial expression.

It is known that there is a common plasma membrane dopamine transporter (DAT) which plays a crucial plays a crucial role in controlling dopamine-mediated neurotransmission and is involved in neurotoxicity. and the manifestation of a number of CNS disorders, including Parkinson disease.

Clinical example 69-year-old man with a ten-year history of Parkinson's disease. Moderate to severe motor symptoms with muscle rigidity, resting tremor, brady-kinesia and slowing of speech. No evidence of dementia or depression. Commenced on 12.5 mg of phenytoin within 2 to 3 days noted improved verbal fluency, enhanced and less effortful social connection and eye contact. An enhanced initiation of movement. Also described an improved perception of efficiency in thought and action. No evidence of loss of efficacy of medication. Using infrared eye tracking technology it was noted that the fixations and saccadic eye movements were enhanced after treatment. Measurements were undertaken both whilst silent and speaking with and without eye contact with the investigator. Based on these investigations in Parkinson's disease and also in mild cognitive impairment and dementia we consider that condition is described as Parkinson plus diseases, including multiple system atrophy (MSA), progressive supranuclear palsy (PSP), corticobasal degeneration (CBD), and dementia with Lewy bodies (DLB)s may also benefit from the addition of a low dose AED with and without a psychostimulant.

Example 19—Personality Disorders

The general diagnostic criterion for personality disorder includes an enduring and rigid pattern of inner experience, thoughts and behaviour that deviates markedly from the expectations of the individual's culture. This pattern of inner experience and behaviour is manifest in the following areas: Cognition; Affectivity; Interpersonal functioning; and Impulse control.

This enduring pattern is inflexible and pervasive across a broad range of personal and social situations and leads to clinically significant distress or impairment in social, occupational, and other important areas of functioning. The pattern is stable and of long duration and onset can often be traced back to at least adolescence or early adulthood. The areas of impairment and functioning are the very ones that appear to improve on treatment with low dose anti-epileptic drugs. The individual's perception of the world is determined by the organisation, integration and prioritisation of information and sensory stimuli and therefore subsequently impact on cognitive functioning. Treatment with a low dose anti-epileptic drug, an individual's approach to the world would be more flexible with an enhanced ability to learn from past experiences in an adaptive manner. Individuals would be able to adapt and benefit from their past experiences—both positive and negative. The manifestations of their personality disorders that previously were longstanding and dysfunctional would begin to abate, with beneficial outcomes to all aspects of their lives.

Example 20—Mild Cognitive Impairment (MCI) and Dementia

Mild cognitive impairment (MCI), also known as incipient dementia, or isolated memory impairment, is a diagnosis given to individuals who have cognitive impairments beyond that expected for their age and education, but that do not interfere significantly with their daily activities. It is considered to be the boundary or transitional stage between normal aging and dementia. MCI can present with a variety of symptoms, but when memory loss is the predominant symptom it is termed "amnesic MCI" and is frequently seen as a risk factor for Alzheimer's disease. Studies suggest that these individuals tend to progress towards probable Alzheimer's disease at a rate of approximately 10% to 15% per year.

There is no proven treatment or therapy for mild cognitive impairment. As MCI may represent a prodromal state to clinical Alzheimer's disease, treatments proposed for Alzheimer's disease, such as antioxidants and cholinesterase inhibitors, may be useful. In fact, several potential treatments are currently under investigation. Two drugs used to treat Alzheimer's disease have been explored in particular, for their ability to effectively treat MCI or prevent/slow down the progress towards full Alzheimer's disease. Rivastigmine failed to stop or slow progression to Alzheimer's disease or improve cognitive function for individuals with MCI, and Donepezil showed only minor, short-term benefits and was associated with significant side effects. Recently, there have been favourable reports regarding Colostrinin, which confirm the drug offers a viable treatment for MCI.

We also consider and have noted individuals with an history of a head injury demonstrated improvement in cognitive functioning of the commencement of a low dose AED with and without the psychostimulant. A 56 year old woman, no history of ADHD in childhood. Involved in a serious motor vehicle accident the age of 29 with a depressed skull fracture and frontal lobe involvement. Subsequent history consistent with a acquired syndrome of ADHD. Subsequent development of co-morbid diagnoses included in alcohol dependence, pathological gambling and major depression. Poor response to antidepressant therapy. Benefited from trial of dexamphetamine 50 mg, later augmented with sodium valproate 150 mg, loss of benefit above this dose. Improved social interaction and egocentric eye gaze. Sustained remission of pathological gambling and alcohol dependence.

An 86-year-old married man with a history of good cognitive functioning until last 4-5 yrs when noted by both his wife and himself to becoming increasingly socially withdrawn primarily because of the difficulty in listening without distraction during social interaction, no known childhood or adult history of prior attentional or impulsive disorders. It has been clinically observed by the inventor that individuals treated with low dose antiepileptic were enhanced in their ability to discriminate irrelevant from the relevant sound was enhanced. He was commenced on a low dose of phenytoin 12.5 mg daily, it was unexpectedly noticed by his wife that he was able to socially interact in a more meaningful way van had been evident for the previous 10 years. The dose was subsequently increased to 25 mg. Over a period of 6 to 8 weeks there was a loss of the benefits which had been previously noted. On ceasing the medication there was an initial improvement again over the preceding 3 to 7 days followed by a loss of the therapeutic effects and returned to his pre-medication function. On the ressumption of the 12.5 mg phenytoin there was a return of the improved function. On this second occasion he was more aware of the benefits and also the gradual return of the detrimental clinic effects. During the clinical assessment it was noted that he had more flexibility in his conversation and more natural use of non-verbal cues, there was also enhancement of his egocentric gaze. With the beneficial effects noted on the phenytoin a trial of low dose sodium valproate 40 mg was also instigated. Similar benefits were noted with an enhanced ability to follow the train of conversation and prevent the distraction of inappropriate intrusions into his conversation. These benefits were also noted by his wife. An increase of the dose to 80 mg sodium valproate resulted in a loss of these benefits. This second trial was then augmented with the phenytoin 10 mg resulted in him and more robust improvement on either medication alone. Again these medications were ceased resulting in a loss of associated benefits. With each trial of medication he became more apparent to the patient and his wife of the benefits of the therapy. He attempted whilst not taking the medication to communicate and follow the conversation in a way that he had been able to whilst on treatment. He found when attempting to do so he became mentally exhausted and unable to sustain the effort required for the interaction. The improvements noted clinically and also recorded using the Developmental Eye Movement test and a measure of parietal function the Alzheimer's Quick Test.

65-year-old married woman diagnosed with fronto-temporal dementia. she had been assessed by neuropsychologist, and geriatrician and psychiatrist to confirm this diagnosis. She did not meet the criteria for Alzheimer's type dementia. She demonstrated emotional dysregulation, word finding difficulties; her speech was empty, non-fluent and laboured. She then relied on others to make decisions for herself. She had gradually become socially disengaged finding such interactions distressing and demanding. On commencement of 25 mg phenytoin she and her husband described a remarkable improvement in her cognitive functioning. Despite ongoing difficulties of word finding she was able to socially interact more spontaneously than she had done for many years. And have confidence in areas of conversation that she previously would have avoided. She was also assessed using a measure of rapid automatic naming and parietal function, The Alzheimer's Quick Test (AQT) which both demonstrated a significant improvement in her functioning on commencement of the phenytoin. On two occasions the medication was withdrawn and then reintroduced, due to the experimental nature of treatment and concern that there might be a significant placebo effect. On each occasion the loss of benefit and its return were closely related to the treatment with phenytoin. There was a two week period where the phenytoin dose was increased to 50 mg. This was associated with loss of the therapeutic benefit and general impairment. Following the subsequent reduction there was a return of the improvement previously noted.

The pattern of impairment to cognitive functioning is consistent with individuals who have benefited from low dose anti-epileptic. The beneficial effects that are noted on commencement of this combination can be further enhanced, synergistically, by the use of a psycho-stimulant. These individuals may or may not meet the full criteria for a DSM IV diagnosis consistent with ADHD. However, we have found that individuals with a sub threshold diagnosis of ADHD can benefit from the use of low dose psycho-stimulants with the low dose anti-epileptic drug.

It is postulated that the use of a low dose anti-epileptic drug has enabled an improvement in cognitive processing and higher executive functioning. The usually well developed and sophisticated ability to maintain social relationships is one of the last systems to reach maturity in adolescence. It would seem therefore reasonable to expect this system to be the most sensitive to any cognitive decline. If treatment were available that could reverse or stabilise the decline, it would have a profound impact and benefit both for the individual's mental health and independence, as well as a delay in the need for more intensive and costly residential care. The benefits seen in this clinical situation would not be expected from the normal and excepted use of an anti-epileptic drug, which normally acts as a general cerebral depressant or mood stabiliser and at a dose that would normally be expected to result in exacerbation of any cognitive impairment, in contrast to the compositions and methods of the invention. It has also been noted in other types of dementia for example in multiple sclerosis there is a slowing of processing evening before the dementia is evident. This can be measured relatively early in the illness and the individual may be otherwise asymptomatic. It is hypothesised that as the inventor has noted improvement in the processing of individuals with MCI and dementia and with a low dose of the AED's together with or without a psychostimulant may improve the cognitive impairment associated with multiple sclerosis and may also enhance overall processing leading to improved psycho social function. We have also noted that the clinical tool used in some research studies to analyse processing speed in multiple sclerosis is The Paced Auditory Serial Addition Test (PASAT) is a measure of cognitive function that specifically assesses auditory information processing speed and flexibility, we have used this tool experimentally in individuals with ADHD and cognitive impairment and demonstrated improvement following treatment with low-dose AED's Example 21—Prevention and Treatment of Psychotic Disorders In one embodiment, the present invention relates to the preventative or proactive treatment of individuals with psychotic disorders, with an anti-epileptic drug, optionally in combination with psycho-stimulants, to improve quality of life outcomes in such individuals. The present invention relates to the treatment of individuals with DSM-IV-TR classified disorders in the schizophrenic cluster, namely schizophrenia, schizoaffective disorder, and drug induced psychosis.

Schizophrenia is typically a late onset disorder characterized by abnormalities in the perception or expression of reality. It is distinguished by symptoms of auditory hallucinations, paranoid or bizarre delusions and thought disorder. People with a schizophrenic disorder may also present with a blunted affect and emotion, poverty of speech, inability to experience pleasure, and a lack of motivation. Further symptoms include chaotic speech, thought and behaviour. Onset of symptoms most commonly occurs in late adolescence and young adulthood. Schizophrenic disorders are primarily thought to affect cognition, but they also usually contribute to chronic problems with behaviour and emotion. This in turn impacts on the person's ability to function in social and occupational settings, contributing to poor quality of life outcomes. People diagnosed with a schizophrenic disorder are likely to present with co-morbid conditions, including depression, anxiety disorders and substance abuse. Average life expectancy for this population is 10 to 12 years less than the average rate, due to poor general health and a high suicide rate. Life-long social problems for a person diagnosed with a schizophrenic disorder include unemployment, social isolation and withdrawal, poverty and homelessness.

Although a direct cause has been difficult to establish, a number of factors have been posited as contributing towards the development of a schizophrenic disorder. Research highlights links between such factors and the onset, development and maintenance of schizophrenic disorders. These factors range from the heritability of schizophrenia, prenatal exposure to infections, social disadvantage (e.g. due to poverty, family dysfunction, unemployment), substance use, abnormal neural functioning and a number of psychological mechanisms. Additionally, a number of psychological mechanisms involving cognitive biases have been identified as potential traits of the pre-onset phase of schizophrenia. These cognitive biases include excessive attention to potential threats, jumping to conclusions, making external attributions, impaired reasoning about social situations and mental states, and difficulties with early visual processing and maintaining concentration.

Treatment of schizophrenic disorders is predominantly pharmacotherapy with anti-psychotic medications, which primarily work by suppressing dopamine activity. Psychotherapy, vocational and social rehabilitation are also key elements in the management of schizophrenic disorders. Periods of hospitalisation may also be necessary at times, particularly when there is a risk to self and others. Treatment generally targets the management of symptoms and improving function, rather than trying to cure the person. It has been suggested that early treatment in the pre-onset phase of psychotic disorders and affective disorders could be most effective, potentially leading to improved functioning and the prevention of more serious morbidity. To maximise this potential and minimise the effect and life-long impact of schizophrenic disorders, there has been much work to identify and treat this pre-onset phase of the illness, which has been detected up to 30 months before the onset of psychotic symptoms.

The present invention provides a method of treating individuals both before and during the pre-onset phase of a serious psychiatric disorder, such as schizophrenia, schizoaffective disorder, and other associated psychoses, which may reduce or in part eliminate certain clinical features, or minimise the severity of psychotic episodes. The present invention is held to improve overall quality of life outcomes for individuals identified with a schizophrenic disorder by improving social cognition and social interaction, and higher executive functioning. It is proposed that improving an individual's ability to connect with others and maintain a positive social network will assist the individual in maintaining a level of psychological resilience. It has been reported that a significant prognostic marker is the presence of a range of supportive people, available to the individual identified with a psychotic disorder such as schizophrenia. Hence, if such a support network can be more closely and positively engaged by the individual, due to improved social cognition and executive functioning, then the resources available to the individual will be markedly increased.

A number of potential trait markers have been identified in the pre-onset phase of schizophrenia, which may be associated with the development of adult psychiatric disorders and are currently being investigated in the research. They include impaired social cognition, impairment of higher executive functioning, nonverbal learning disorders and abnormal eye movements. Some of these markers have also been associated with pervasive developmental disorders and attention deficit disorder (with hyperactivity). Unfortunately however, these markers cannot be considered reliable in predicting the later development of schizophrenia, at this stage. Another favourable line of current research is investigating the combination of genetic risk plus reported experiences of non-disabling, psychosis-like events as a possible predictor of later diagnosis.

The presence of these two factors (family history of schizophrenia and the presence of transient or self-limiting psychotic experiences) place people in the 'ultra high-risk mental state' criteria. People who fulfill the 'ultra high-risk mental state' criteria, are considered to have a 20-40% chance of being diagnosed with schizophrenia after one year. The use of psychological treatments and medication has been found effective in reducing the chances of people in the 'high-risk' category, from developing full-blown schizophrenia. However, the consequent treatment of people who may never develop schizophrenia is controversial. Potential side-effects of traditional antipsychotic medication include the potentially disfiguring tardive dyskinesia and the rare but potentially lethal neuroleptic malignant syndrome.

The present invention provides a safer and measurable therapeutic intervention for individuals identified in the high-risk category. It is proposed that the present invention of providing an anti-epileptic drug at what is normally considered sub-therapeutic levels, to individuals identified in the high-risk category for later developing schizophrenia, will produce improved functioning amongst these individuals and provide measurable relief from presenting symptoms and traits. This benefit would be equally available to individuals who might or might not later develop a psychiatric disorder such as schizophrenia. However, in addition to treating an individual's presenting difficulties, it is further proposed that the present invention has the potential benefit of preventing a future psychotic illness. It should be noted that the use of an anti-epileptic drug, which are clinically well understood and have a long term safety record especially in their use with children and young adolescents, makes the present invention particularly attractive as a therapeutic intervention.

It has been stated in this paper, that improving an individual's ability to connect with others and maintain a positive social network, will assist the individual in maintaining a level of psychological resilience, despite the presence of a psychiatric disorder. Impairment of social cognition and social discourse is a feature of a number of psychiatric disorders, including but not exclusive to schizophrenia, bipolar, and general anxiety disorders. Impairment of social cognition often leads to a breakdown in an individual's social networks, availability of supportive resources and a general deterioration of the person's sense of self worth.

An essential aspect of social cognition, in establishing and maintaining a sense of connectedness during social interactions is the ability to sustain eye gaze. There are many subtleties in proficiently gauging and interpreting verbal and nonverbal communication during social discourse. Social discourse always involves at least two communicative partners. It is a fluid interaction between the tasks of speaking and listening—sharing and understanding each others' ideas and thoughts. Underlying the verbal interaction between the communicative partners is the subtle interplay and reciprocity of a sophisticated non-verbal communication system. Competent communicators tune into the nonverbal signals of their partner without consciously thinking about it. It can be quite an instinctual process. However, missed cues or misperceived nonverbals can disrupt the entire flow of a conversation and cause irreparable breakdown in the social discourse. This subtle interplay between speaker and listener consists of communicative nonverbal behaviours such as eye gaze, facial gestures (e.g. smiling; looking interested), nodding assent and comprehension, vocalisations (e.g. "ah-hah"; "hmmm"), simple verbal encouragement (e.g. "I see"; "Right") to more complex verbal skills (e.g. asking appropriate questions; seeking clarification). Together, these nonverbal and verbal behaviours tend to signal a general message of—"It's OK, I'm with you, I understand." There is a sense that both speaker and listener are 'on the same page'. However, not only is shared comprehension signalled between the communicative partners, but also a general sense of engagement or social connectedness. These underlying messages of social connection are largely expressed through the nonverbals and received visually via eye gaze. Abnormal eye gaze disrupts the flow of the interchange—both from the speaker's perspective and the listener's.

Abnormal gaze and eye movements have been identified in individuals diagnosed with schizophrenia and other disorders such as autism, ADHD, learning difficulties, and Parkinson's. The mechanisms involved in eye movements such as gaze, tracking and saccadic movements have been further related to the efficiency of cognitive processing and higher executive function, which in turn are required for effortless and effective social interaction. It is believed that the abnormal eye movements identified in individuals with schizophrenia occurs as a consequence of a deficit that is not restricted to the ocular motor system. It has been demonstrated that the deficit in the representational guidance of behaviour is independent of the motor system itself. This impairment in the processing may be indirectly or directly related to the impaired cognitive processes that could contribute to the development of the psychotic illness itself.

The ocular motor delayed response task highlights evidence of deficits in working memory, which in turn suggests the existence of prefrontal pathology in individuals with schizophrenia. This dysfunction in the pre-frontal cortex has also been implicated in identified abnormalities of smooth pursuit eye movement (SPEM), present in many schizophrenic patients and their first degree relatives. Research is investigating the full role of the pre-frontal cortex in inhibiting the saccadic system while the smooth pursuit system is activated, and the proposed relationship between smooth pursuit eye movement dysfunction and weakened frontal control over lower motor systems. Research has found a significant correlation between SPEM abnormalities and working memory dysfunction within individuals diagnosed with a schizophrenic disorder. It is further noted that the dorsal lateral prefrontal cortex mediates both SPEM and working memory.

The high prevalence of eye movement dysfunction (EMD) among psychotic patients is one of the few consistently replicated findings concerning psycho-physiological factors that accompany the idiopathic psychosis. Although reported prevalence rates of EMD's vary, the average appears to be about 60% in populations of schizophrenic patients, about 40% in populations of bipolar affective disorders, and about 8% in the normal population. EMD is also found in approximately 45% of unaffected first-degree relatives of schizophrenic patients and in about 12% of the unaffected relatives of bipolar patients.

Research has also noted that cerebral depressants including anti-epilepsy, administered at usual therapeutic doses affect the morphology of smooth pursuit eye movements. This disruption of the eye movements appears to be dose related as previous investigations have applied the usual therapeutic doses for bipolar disorder and epilepsy. These investigations do not appear to have been replicated at low or very low doses, as is proposed in the present invention. We propose that with the clinically observed efficacy of these medications to affect the eye movements in individuals with EMD and higher executive functioning impairment, the use of low dose treatments would confer a positive therapeutic benefit. We have also noted in our clinical populations that improvements in eye movements and automatic processing often coincide with similar gains in social communication, social functioning and eye gaze.

In our clinical observations, we have further noted a significant change in the speed and efficiency of vertical and horizontal number calling ability with the administration of low dose anti-epileptic drugs which fall markedly below the usual therapeutic range. (Number calling ability is a simple clinical measure of an integrative and automatic processing and the efficiency of eye tracking movements.) We have also noted changes in number calling from a horizontal spatial array, which requires a more sophisticated level of ocular motor control. Both these measurements have been shown to improve together and independently. The effects appear to be reversible as when the medication is ceased the benefit is lost and recommencement of the medication sees the return of the improvements.

From our clinical observations and experimental understanding of the effect of low dose anti-epileptic drugs on both saccadic and tracking eye movements, we would extrapolate that there will be an enhancement of eye gaze in social settings, with predictable improvement in higher executive functioning. Such a proposal has been supported through changes noted by the clinician of an individual's behaviour and the individual's self-report during clinical sessions. We have also noted in the clinic that the beneficial effects that are noted on commencement of this combination can be further enhanced, synergistically, by the use of a psycho-stimulant. These individuals may or may not meet the full criteria for a DSM IV diagnosis consistent with ADHD. However, we have found that individuals with a subthreshold diagnosis of ADHD can benefit from the use of low dose psycho-stimulants with the low dose anti-epileptic drug.

It is proposed that by improving eye movements such as gaze and tracking, an individual would be able to focus more specifically on important aspects within the visual field— namely the person to whom they are speaking and their nonverbal communications. This in turn may produce improved engagement during social interactions, both for the individual with a schizophrenic disorder and a reciprocity by the communicative partner. As a preventative or proactive strategy in the treatment of individuals in the pre-onset phase of a schizophrenic disorder, it would enhance and build social contacts and a supportive network, which might in turn minimise the harm of any subsequent psychotic episode. Therefore, measurement of eye movements could provide the clinician with a vital tool in managing and treating individuals with a schizophrenic disorder or at risk of developing such a disorder. Eye movement measures could provide a clear and objective means of evaluating and monitoring progress through pre- and post-therapeutic intervention.

It has been postulated that eye movements reflect an individual's thought processes; so a person's thoughts and cognitive processing, may be followed to some extent from records of eye movements. This theory has had significant impact in the research investigating social cognition and reading ability.

Another aspect of ocular motor control that has been investigated in the research is in relation to the blink rate. Abnormalities have been identified in the blink rate of individual's diagnosed with a number of psychiatric disorders, including schizophrenia. Our clinical observations have noted improvement in egocentric gaze control in individuals diagnosed with an autistic spectrum disorder, with the commencement of treatment with low dose anti-epileptic drugs. This clinical observation was unexpected and robust. It is suggested that the development of the higher executive function required for the maintenance of egocentric gaze coincides with the acquisition of a more mature eye blink reflex. This has been well described for both normal populations and individuals diagnosed with pervasive development disorders. We therefore propose that the eye blink reflex might prove to be a useful and simple clinical marker for measuring an individual's alteration in cerebral function, on commencing the therapeutic intervention of a low dose of anti-epileptic drug. Possible correlations could then be explored between improvements in the blink reflex and clinical observations of an individual's improved ability to sustain eye gaze during social interactions.

It is proposed that the present invention of providing either an anti-epileptic drug at what is normally considered sub-therapeutic levels, to individuals diagnosed with psychiatric disorders such as schizophrenia, will produce a reduction in both abnormal eye movements and blink rate contributing to an improvement in egocentric gaze. These improvements can be reliably recorded with the use of eye movement, blink or facial tracking technology. These changes can be empirically quantified and related to other observable clinical and social changes in the areas of social cognition and higher executive functioning. We have also noted in the clinic that the beneficial effects that are noted on commencement of this combination can be further enhanced, synergistically, by the use of a psycho-stimulant. These individuals may or may not meet the full criteria for a DSM IV diagnosis consistent with ADHD. However, we have found that individuals with a subthreshold diagnosis of ADHD can benefit from the use of low dose psycho-stimulants with the low dose anti-epileptic drug.

44-year-old woman with her son diagnosed with ADHD, not meeting the full criteria for a diagnosis of ADHD, however significant improvement both from the commencement of dexamphetamine 2.5 mg daily and the latest addition of topiramate 12.5 mg daily. Medication is ceased and recommenced on a number of occasions which was associated loss of improvement and a subsequent return of function and recommencement. Of particular note worth the social benefits including the improvement and the subjective normalisation of egocentric eye gaze and prosody of her conversation. She also described an enhanced ability to more clearly articulate her of thoughts and ideas than she had ever known previously.

We have been able to quantify the improvement in social interaction using Seeing Machines™ facial tracking with the audio recording of the conversation allowing the correlation of the direction of gaze together with the dialogue recording.

The various features and embodiments of the present invention, referred to in individual sections above apply, as appropriate, to other sections, mutatis mutandis. Consequently features specified in one section may be combined with features specified in other sections, as appropriate.

All publications mentioned in the above specification are herein incorporated by reference. Various modifications and variations of the described methods and products of the invention will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in the relevant fields are intended to be within the scope of the following claims.

The invention claimed is:

1. A method of treating a psychiatric disorder which is selected from Mild Cognitive Impairment (MCI) in a subject in need thereof, including the step of administering to the subject one or more anti-epileptic agents selected from: carbamazepine, clobazam, clonazepam, ethosuximide, felbamate, gabapentin, lamotrigine, levetiracetam, oxcarbazepine, phenobarbital, phenytoin, pregabalin, primidone, retigabine, rufinamide, talampanel, tiagabine, topiramate, valproate or derivatives thereof, vigabatrin and zonisamide, or a pharmaceutically acceptable salt thereof, and optionally one or more psychostimulants selected from dexamphetamine and methylphendidate, or pharmaceutically acceptable salt thereof, to thereby treat the psychiatric disorder, wherein the amount of anti-epileptic agent is less than 30% of the daily dose of anti-epileptic agent minimally therapeutic in mood stabilization or treatment of epilepsy or epileptic symptoms.

2. The method of claim 1, wherein a single anti-epileptic agent is administered.

3. The method of claim 1, wherein two or more anti-epileptic agents are administered.

4. The method of claim 1, wherein the amount of anti-epileptic agent is less than 20% of the daily dose of anti-epileptic agent minimally therapeutic in mood stabilization or treating epilepsy or epileptic symptoms.

5. The method of claim 1, wherein the anti-epileptic agent is selected from: valproate or derivatives thereof, rufinamide, topiramate, and phenytoin.

6. The method of claim 1, wherein the anti-epileptic agent, or a pharmaceutically acceptable salt thereof, and the psychostimulant, or pharmaceutically acceptable salt thereof, are administered in the form of a pharmaceutical composition comprising, in combination, one or more anti-epileptic agents, or a pharmaceutically acceptable salt thereof, and one or more psychostimulants, or pharmaceutically acceptable salt thereof; together with a pharmaceutically acceptable carrier, diluent and/or excipient; wherein the amount of anti-epileptic agent is less than 30% of the daily dose of anti-epileptic agent minimally therapeutic for mood stabilization, treatment of epilepsy or epileptic symptoms.

7. The method of claim 1, including the step of administering to the subject one or more anti-epileptic agents, or a pharmaceutically acceptable salt thereof, and one or more psychostimulants, or pharmaceutically acceptable salt thereof, to thereby treat the psychiatric disorder, wherein the amount of anti-epileptic agent is less than 30% of the daily dose of anti-epileptic agent minimally therapeutic in mood stabilization or treatment of epilepsy or epileptic symptoms.

8. The method of claim 1, wherein the method comprises treating an impairment or deficiency in higher order executive functioning associated with the psychiatric disorder.

9. The method of claim 1, wherein the anti-epileptic agent is phenytoin and the amount of anti-epileptic agent is daily dose of less than 60 mg.

10. The method of claim 1, wherein the anti-epileptic agent is sodium valproate and the amount of anti-epileptic agent is a daily dose of less than 120 mg.

11. The method of claim 1, wherein one or more psychostimulant or pharmaceutically acceptable salt thereof is administered.

* * * * *